US010005797B2

(12) United States Patent
Nagashima et al.

(10) Patent No.: US 10,005,797 B2
(45) Date of Patent: Jun. 26, 2018

(54) HYDROSILYLATION REACTION CATALYST

(71) Applicants: KYUSHU UNIVERSITY, NATIONAL UNIVERSITY CORPORATION, Fukuoka-shi, Fukuoka (JP); SHIN-ETSU CHEMICAL CO., LTD., Tokyo (JP)

(72) Inventors: Hideo Nagashima, Fukuoka (JP); Yusuke Sunada, Fukuoka (JP); Atsushi Tahara, Fukuoka (JP); Daisuke Noda, Fukuoka (JP); Hiroe Soejima, Fukuoka (JP); Koji Sakuta, Annaka (JP)

(73) Assignees: KYUSHU UNIVERSITY, NATIONAL UNIVERSITY CORPORATION, Fukuoka-Shi, Fukuoka (JP); SHIN-ETSU CHEMICAL CO., LTD., Tokyo (JP)

( * ) Notice: Subject to any disclaimer, the term of this patent is extended or adjusted under 35 U.S.C. 154(b) by 0 days. days.

(21) Appl. No.: 15/503,209

(22) PCT Filed: Aug. 12, 2015

(86) PCT No.: PCT/JP2015/072830
§ 371 (c)(1),
(2) Date: Feb. 10, 2017

(87) PCT Pub. No.: WO2016/024607
PCT Pub. Date: Feb. 18, 2016

(65) Prior Publication Data
US 2017/0233417 A1 Aug. 17, 2017

(30) Foreign Application Priority Data
Aug. 12, 2014 (JP) .................. 2014-164181

(51) Int. Cl.
*C07F 7/04* (2006.01)
*C07F 7/08* (2006.01)
*B01J 31/22* (2006.01)

(52) U.S. Cl.
CPC ......... *C07F 7/0879* (2013.01); *B01J 31/2208* (2013.01); *B01J 31/2273* (2013.01); *B01J 2231/323* (2013.01); *B01J 2531/821* (2013.01); *B01J 2531/842* (2013.01); *B01J 2531/845* (2013.01)

(58) Field of Classification Search
CPC ................ C07F 7/0829; B01J 31/2208; B01J 2231/323; B01J 2231/2273; B01J 2531/82; B01J 2531/84
USPC ...................................................... 556/456
See application file for complete search history.

(56) References Cited

U.S. PATENT DOCUMENTS

| 4,992,573 A | 2/1991 | Lewis |
| 5,389,404 A | 2/1995 | Armstrong |
| 5,523,436 A | 6/1996 | Dauth et al. |
| 5,561,231 A | 10/1996 | Dauth et al. |
| 6,124,418 A | 9/2000 | Crivello et al. |
| 6,303,728 B1 | 10/2001 | Hagimori et al. |
| 6,492,525 B1 | 12/2002 | Bertrand et al. |
| 6,803,440 B2 | 10/2004 | Marko et al. |
| 7,563,741 B2 | 7/2009 | Brummer et al. |
| 7,803,893 B2 | 9/2010 | Hofmann et al. |
| 8,124,711 B2 | 2/2012 | Hofmann et al. |
| 8,236,915 B2 | 8/2012 | Delis et al. |
| 8,415,443 B2 | 4/2013 | Delis et al. |
| 8,895,770 B2 | 11/2014 | Lewis et al. |
| 9,073,950 B2 | 7/2015 | Kownacka et al. |
| 9,480,977 B2 | 11/2016 | Brandstadt et al. |
| 2014/0249311 A1 | 9/2014 | Brandstadt et al. |

FOREIGN PATENT DOCUMENTS

| JP | 1-315344 A | 12/1969 |
| JP | 6-136126 A | 5/1994 |
| JP | 6-263780 A | 9/1994 |
| JP | 7-149780 A | 6/1995 |
| JP | 2001-131231 A | 5/2001 |
| JP | 3174616 B2 | 6/2001 |
| JP | 3599669 B2 | 12/2004 |
| JP | 3854151 B2 | 12/2006 |
| JP | 4007467 B2 | 11/2007 |
| JP | 4249702 B2 | 4/2009 |
| JP | 4934190 B2 | 5/2012 |
| JP | 5032561 B2 | 9/2012 |
| JP | 2012-532884 A | 12/2012 |
| JP | 2012-532885 A | 12/2012 |
| JP | 2013-544624 A | 12/2013 |
| JP | 2014-502271 A | 1/2014 |
| JP | 2014-503507 A | 2/2014 |
| WO | WO 2010/016416 A1 | 2/2010 |
| WO | WO 2013/043783 A2 | 3/2013 |
| WO | WO 2013/043785 A2 | 3/2013 |
| WO | WO 2013/043787 A2 | 3/2013 |
| WO | WO 2013/043846 A1 | 3/2013 |
| WO | WO 2013/043912 A2 | 3/2013 |
| WO | WO 2013/081794 A1 | 6/2013 |
| WO | WO 2014/021908 A1 | 2/2014 |

OTHER PUBLICATIONS

Adams, K. Paige et al., "The Catalytic Activity of Transition Metal Complexes of Sterically Hindered Isocyanides", Journal of Molecular Catalysis, 1985, vol. 29, pp. 201-208.*
Adams et al., "The Catalytic Activity of Transition Metal Complexes of Sterically Hindered Isocyanides", Journal of Molecular Catalysis, 1985, vol. 29, pp. 201-208.

(Continued)

*Primary Examiner* — Sudhakar Katakam
*Assistant Examiner* — Kofi Adzamli
(74) *Attorney, Agent, or Firm* — Birch, Stewart, Kolasch & Birch, LLP

(57) ABSTRACT

A hydrosilylation reaction catalyst prepared from: a catalyst precursor comprising a transition metal compound, excluding platinum, belonging to group 8-10 of the periodic table, e.g., iron acetate, cobalt acetate, nickel acetate, etc.; and a ligand comprising an isocyanide compound such as t-butyl isocyanide. The hydrosilylation reaction catalyst has excellent handling and storage properties. As a result of using this catalyst, a hydrosilylation reaction can be promoted under gentle conditions.

8 Claims, 3 Drawing Sheets

(56) References Cited

OTHER PUBLICATIONS

Bart et al., "Preparation and Molecular and Electronic Structures of Iron(0) Dinitrogen and Silane Complexes and Their Application to Catalytic Hydrogenation and Hydrosilation", J. Am. Chem. Soc., 2004, vol. 126, pp. 13794-13807.
Brookhart et al., "Mechanism of a Cobalt(III)-Catalyzed Olefin Hydrosilation Reaction: Direct Evidence for a Silyl Migration Pathway", J. Am. Chem. Soc. 1993, vol. 115, pp. 2151-2156.
Chalk et al., "Dicobalt Octacarbonyl as a Catalyst for Hydrosilation of Olefins", J. Am. Chem. Soc., 1965, vol. 87, No. 16, pp. 1133.
Chalk et al., "Homogeneous Catalysis. IV. Some Reactions of Silicon Hydrides in the Presence of Cobalt Carbonyls", Journal of the American Chemical Society, Mar. 29, 1967, vol. 89, No. 7, pp. 1640-1647.
Chalk, "The Hydrosilation of Olefins Catalyzed by Some Rhodium and Cobalt Complexes", Journal of Organometallic Chemistry, 1970, vol. 21, pp. 207-213.
Chatani et al., "The $CO_1(CO)_1$-Catalyzed Hydrosilylation of Oxygen-Containing Olefins: Silylmetalation as a Key Step", Chemistry Letters, 2000, pp. 14-15.
Cornish et al., "Homogeneous Catalysis VI . Hydrosilylation using Tris(Pentanedionato)Rhodium(III) or Tetrakis(μ-Acetato)Dirhodium(II) as Catalyst", Journal of Organometallic Chemistry, 1979, vol. 172, pp. 153-163.
Hill et al., "Rhodium Carbene Complexes as Hydrosilylation Catalysts", Journal of Organometallic Chemistry, 1977, vol. 137, pp. 293-300.
Hyder et al., "Oligomerization and regioselective hydrosilylation of styrenes catalyzed by cationic allyl nickel complexes bearing allylphosphine ligands", Dalton Trans., 2007, pp. 3000-3009.
Imlinger et al., "Rh(1,3-bis(2,4,6-trimethylphenyl)-3,4,5,6-tetrahydropyrimidin-2-ylidene)(COD) tetrafluoroborate, an unsymmetrical Rh-homoazalylcarbene: synthesis, X-ray structure and reactivity in carbonyl arylation and hydrosilylation reactions", Journal of Organometallic Chemistry, 2005, vol. 690, pp. 4433-4440.
International Search Report, issued in PCT/JP2015/072830 (PCT/ISA/210), dated Nov. 10, 2015.
Ito et al., "Synthesis of New Bulky Isocyanide Ligands and Their Use for Rh-catalyzed Hydrosilylation", Chemistry Letters, 2006, vol. 35, No. 9, pp. 1038-1039, ISSN 0366-7022, particularly, Abstract, p. 1038, right column, 2nd paragraph, Scheme 1, Table 1.
Junquera et al., "R-Allyl Nickel(II) Complexes with Chelating N-Heterocyclic Carbenes: Synthesis, Structural Characterization, and Catalytic Activity", Organometallics, 2012, vol. 31, pp. 2175-2183.
Kakiuchi et al., "Completely selective synthesis of (E)-β-( triethylsilyl)styrenes by $Fe_8(CO)_\alpha$-catalyzed reaction of styrenes with triethylsilane", Journal of Organometallic Chemistry, 1993, vol. 456 , pp. 45-47.
Kamata et al., "Catalytic Hydrosilylation of Alkenes by Iron Complexes Containing Terpyridine Derivatives as Ancillary Ligands", Organometallics, 2012, vol. 31, pp. 3825-3828.
Kiso et al., "Silicon Hydrides and Nickel Complexes I. Phosphine-Nickel(II) Complexes as Hydrosilylation Catalysts", Journal of Organometallic Chemistry,1973, vol. 50, pp. 297-310.
Li et al., "Synthesis of rhodium N-heterocyclic carbene complexes and their catalytic activity in the hydrosilylation of alkenes in ionic liquid medium", Journal of Organometallic Chemistry, 2011, vol. 696, pp. 2116-2121.
Lipschutz et al., "Synthesis and reactivity of a conveniently prepared two-coordinate bis(amido) nickel(II) complex", Chem. Commun., 2012, vol. 48, pp. 7146-7148.
Maciejewski et al., "Catalysis of hydrosilylation Part XXXIV. High catalytic efficiency of the nickel equivalent of Karstedt catalyst $[(Ni(\eta-CH_8=CHSiMe_3),O],[\mu-(\eta-CH_8=CHSiMe_3),O)]$", Journal of Organometallic Chemistry, 2000, vol. 597, pp. 175-181.
Magomedov et al., "Hydrosilylation of Olefins in the Presence of Metal Carbonyls", Journal of Organometallic Chemistry, 1978, vol. 149, pp. 29-36.
Mo et al., "Anchoring of Silyl Donors on a N-Heterocyclic Carbene through the Cobalt Mediated Silylation of Benzylic C-H Bonds", Angewandte Chemie. International Edition, 2013, vol. 52, pp. 10845-10849.
Naumov et al., "Selective Dehydrogenative Silylation-Hydrogenation Reaction of Divinyldisiloxane with Hydrosilane Catalyzed by an Iron Complex", Journal of the American Society, 2012, vol. 134, pp. 804-807.
Nesmeyanov et al., "Addition, Substitution, and Telomerization Reactions of Olefins in the Presence of Metal Carbonyls or Colloidal Iron", Tetrahedron, 1962, vol. 17, pp. 61-68.
Reichel et al., "Photochemistry of Cobalt Carbonyl Complexes Having a Cobalt-Silicon Bond and Its Importance in Activation of Catalysis", Inorg. Chem., 1960, vol. 19, pp. 3856-3860.
Schroeder et al., "Pentacarbonyliron(0) Photocatalyzed Reactions of Trialkylsilanes with Alkenes", Journal of Organometallic Chemistry, 1977, vol. 128, pp. 345-358.
Suginome et al., "Optically Active Isonitrile Ligand for Palladium-Catalyzed Enantioselective Bis-Silylation of Carbon-Carbon Double Bonds", Tetrahedron Letters, 1997, vol. 38, No. 4, pp. 555-558, ISSN 0040-4039, particularly, Abstract, p. 555, 3rd paragraph, p. 556, 2nd paragraph, Scheme 2.
Takeshita et al., "The Catalyzed Reaction of α,β-Unsaturated Esters with Various Hydrosilanes", J. Org. Chem., 1987, vol. 52, pp. 4864-4868.
Tondreau et al., "Iron Catalysts for Selective Anti-Markovnikov Alkene Hydrosilylation Using Tertiary Silanes", Science, 2012, vol. 335, pp. 567-570.
Tondreau et al., "Synthesis, Electronic Structure, and Alkene Hydrosilylation Activity of Terpyridine and Bis(imino)pyridine Iron Dialkyl Complexes", Organometallics, 2012, vol. 31, pp. 4886-4893.
Truscott et al., "Well-defined NHC-rhodium hydroxide complexes as alkene hydrosilylation and dehydrogenative silylation catalysts", Dalton Transactions, 2013, vol. 42, pp. 270-276.
Written Opinion of the International Searching Authority, issued in PCT/JP2015/072830 (PCT/ISA/237), dated Nov. 10, 2015.

* cited by examiner

HYDROSILYLATION REACTION CATALYST

TECHNICAL FIELD

This invention relates to a hydrosilylation reaction catalyst and more particularly, to a hydrosilylation reaction catalyst formed from a metal compound serving as a catalyst precursor and an isocyanide compound serving as a ligand component.

BACKGROUND ART

Hydrosilylation reaction which is addition reaction of a Si—H functional compound to a compound having a carbon-carbon double bond or triple bond is a useful means for the synthesis of organosilicon compounds and an industrially important synthesis reaction.

As the catalyst for hydrosilylation reaction, Pt, Pd and Rh compounds are known. Among others, Pt compounds as typified by Speier catalyst and Karstedt catalyst are most commonly used.

While several problems arise with reaction in the presence of Pt compounds as the catalyst, one problem is that upon addition of a Si—H functional compound to terminal olefin, a side reaction due to internal rearrangement of olefin takes place. Since this system does not exert addition reactivity to the internal olefin, unreacted olefin is left in the addition product. To drive the reaction to completion, it is necessary to use an excess amount of olefin in advance by taking into account the fraction left as a result of side reaction.

Another problem is that the selectivity of α- and β-adducts is low depending on the type of olefin.

The most serious problem is that all the center metals Pt, Pd and Rh are quite expensive noble metal elements. As metal compound catalysts which can be used at lower cost are desired, a number of research works have been made thereon.

For example, reaction in the presence of iron-carbonyl complexes ($Fe(CO)_5$, $Fe_2(CO)_{12}$) is known from Non-Patent Document 1, although this reaction requires reaction conditions including as high a temperature as 160° C. or light irradiation (Non-Patent Document 2).

For these iron-carbonyl complexes, it is reported in Non-Patent Document 3 and Patent Document 1 that dehydrogenation silylated products are obtained rather than the addition reaction.

Also Non-Patent Document 4 and Patent Document 2 report a reaction of methylvinyldisiloxane and methylhydrogendisiloxane in the presence of an iron-carbonyl complex coordinated with a cyclopentadienyl group. Since dehydrogenation silylation reaction takes place along with the relevant reaction, the selectivity of addition reaction is low.

With respect to reaction in the presence of an iron catalyst having a terpyridine ligand (Non-Patent Document 5), a large excess of a reducing agent ($NaBHEt_3$) is necessary as a reaction co-agent. Although $PhSiH_3$ and $Ph_2SiH_2$ add to olefins, more useful trialkylsilanes, alkoxysilanes and siloxanes have poor addition reactivity to olefins.

Non-Patent Document 6 reports that from reaction in the presence of an iron catalyst having a terpyridine ligand and a bistrimethylsilylmethyl group, an addition reaction product is obtained in high yields. This method needs some steps until the catalyst is synthesized, including first synthesizing a terpyridine-iron complex as a catalyst precursor and introducing a bistrimethylsilylmethyl group therein at a low temperature, which steps are not easy industrially.

Also, Non-Patent Documents 7 and 8 report iron complexes having a bisiminopyridine ligand. It is disclosed that they exhibit high reactivity to alkoxysilanes and siloxanes under mild conditions.

The reaction using the complex, however, suffers from several problems including low reactivity with internal olefin, the use of sodium amalgam consisting of water-prohibitive sodium and highly toxic mercury and requiring careful handling (or use of water-prohibitive $NaBEt_3H$) for complex synthesis, low stability of the complex compound itself, a need for a special equipment like a glove box for handling, and a need for storage in an inert gas nitrogen atmosphere at low temperature.

Non-Patent Documents 9 to 14 report examples of reaction in the presence of cobalt-carbonyl complexes (e.g., $Co_2(CO)_5$), but they are unsatisfactory in reaction yield and reaction molar ratio. No reference is made to addition reactivity to siloxanes.

Also an example of reaction of olefin with trialkylsilane in the presence of a cobalt-carbonyl complex substituted with a trialkylsilyl group is reported in Non-Patent Document 15, but the yield is low and the selectivity is low.

Non-Patent Document 16 reports reaction of olefin with trialkylsilane in the presence of a cobalt-phosphite complex coordinated with a cyclopentadienyl group, and Non-Patent Document 17 reports reaction of olefin with trihydrophenylsilane in the presence of a cobalt complex coordinated with N-heterocyclocarbene. Because of low stability, these complex compounds require a special equipment like a glove box for handling and an inert gas atmosphere and a low temperature for storage.

Also Patent Documents 3 to 6 report iron, cobalt and nickel catalysts having terpyridine, bisiminopyridine and bisaminoquinoline ligands. Like the above-cited Non-Patent Documents 6 to 8, there are problems including industrial difficulty of synthesis of a catalyst precursor or synthesis of the complex catalyst from the precursor, low stability of the complex compound itself, and a need for a special equipment for handling.

Patent Document 7 discloses a method of conducting reaction in the presence of a complex catalyst having a bisaminoquinoline ligand, using Mg(butadiene).2THF or $NaEt_3BH$ as the catalyst activator. There are the same problems as above and the yield of the desired product is less than satisfactory.

Many examples of the nickel complex catalyst are reported. For example, a catalyst having a phosphine ligand (Non-Patent Document 18) lacks in selectivity and requires careful handling and storage.

With a vinylsiloxane-coordinated catalyst (Non-Patent Document 19), a dehydrogenation silylated product becomes predominant, indicating low selectivity of addition reaction.

With an alkylphosphine-coordinated catalyst (Non-Patent Document 20), the yield is low, and trihydrophenylsilane is not a substrate of industrial worth.

A bisamide-bearing catalyst (Non-Patent Document 21) needs careful handling and storage, and dihydrodiphenylsilane is not a substrate of industrial worth.

A catalyst having N-heterocyclocarbene ligand (Non-Patent Document 22) has low selectivity of reaction, and trihydrophenylsilane is not of industrial worth.

Many rhodium complex catalysts are reported. For example, catalysts having a carbonyl or cyclooctadienyl (COD) group and a N-heterocarbene ligand (Non-Patent Documents 23, 24) require handling and storage in an inert gas atmosphere because the complex compounds have low stability.

Non-Patent Document 25 discloses to conduct reaction in the presence of an ionic liquid in order to enhance reactivity. The step of separating the ionic liquid from the reaction product is necessary. Since the catalyst used therein has a COD group and a N-heterocarbene group as the ligand, the same problems as described above are left.

Also Non-Patent Document 26 reports an exemplary catalyst which allows for preferential progress of dehydrogenation silylation reaction.

Furthermore, Non-Patent Document 27 reports an example in which an isocyanide compound is added to a complex catalyst to form a catalyst, which is used in hydrosilylation reaction without isolation. A study on reactivity with three types of silanes shows that the order of reactivity is from dimethylphenylsilane, which gives the highest yield (yield 81%), next triethylsilane (yield 66%), to triethoxysilane (yield 40%). The reactivity with triethoxysilane which is of the most industrial worth among the three types of silanes is not so high, while the reactivity with siloxanes is reported nowhere.

In addition, the precursor catalyst having a COD group as the ligand requires careful handling and storage.

On the other hand, Non-Patent Document 28 reports that a rhodium catalyst having an acetylacetonato or acetate group enables addition reaction of triethoxysilane in high yields.

Although this method has the advantage of easy storage and handling of the catalyst, no study is made on reactivity with siloxanes which are more useful from the industrial standpoint.

In addition, rhodium is likewise an expensive noble metal element. Its catalytic function must be further increased to a higher activity before it can be used in practice as a platinum replacement.

The catalysts with their application to organopolysiloxanes being borne in mind include a catalyst having a phosphine ligand (Patent Document 8), a catalyst having an aryl-alkyl-triazenide group (Patent Document 9), a colloidal catalyst (Patent Document 10), a catalyst coordinated with a sulfide group (Patent Document 11), and a catalyst coordinated with an amino, phosphino or sulfide group and an organosiloxane group (Patent Document 12).

However, reactivity is empirically demonstrated with respect to only platinum, palladium, rhodium and iridium which are expensive metal elements. Thus the method is not regarded cost effective.

In Examples of Patent Documents 13 and 14, only well-known platinum catalysts are demonstrated to exert a catalytic effect while the structure which is combined with another metal to exert catalytic activity is indicated nowhere.

Patent Documents 15 to 17 disclose catalysts coordinated with carbene. Patent Document 15 does not discuss whether or not the catalyst is effective to hydrosilylation reaction.

Patent Documents 16 and 17 disclose catalysts coordinated with carbene and vinylsiloxane, but describe only platinum catalysts in Examples.

In addition, the metal catalysts coordinated with carbene require careful handling because the complex compounds have low storage stability.

Patent Documents 18 and 19 disclose ruthenium catalysts coordinated with $\eta^6$-arene or $\eta^6$-triene. These catalysts have inferior reactivity to platinum catalysts and require careful handling because the complex compounds have low storage stability.

Patent Documents 20 to 26 disclose a method of mixing a metal salt with a compound which coordinates to the metal and using the product as a catalyst rather than the use of metal complexes as the catalyst. Although these Patent Documents describe the progress of hydrosilylation with several exemplary combinations, the yield and other data are described nowhere, and the extent to which the reaction takes place is not evident. Although all Examples use ionic salts and hydride reducing agents as the activator, catalytic activity is not detected in most Examples.

PRIOR ART DOCUMENTS

Patent Documents

Patent Document 1: WO 2013/081794
Patent Document 2: WO 2010/016416
Patent Document 3: JP-A 2012-532885
Patent Document 4: JP-A 2012-532884
Patent Document 5: JP-A 2013-544824
Patent Document 6: JP-A 2014-502271
Patent Document 7: JP-A 2014-503507
Patent Document 8: JP-A H06-136126
Patent Document 9: JP-A H06-263780
Patent Document 10: JP-A H01-315344
Patent Document 11: JP 3174616
Patent Document 12: JP-A H07-149780
Patent Document 13: JP-A 2001-131231
Patent Document 14: JP 4007467
Patent Document 15: JP 3599669
Patent Document 16: JP 3854151
Patent Document 17: JP 4249702
Patent Document 18: JP 4934190
Patent Document 19: JP 5032561
Patent Document 20: WO 2013/043846
Patent Document 21: WO 2013/043783
Patent Document 22: WO 2013/043912
Patent Document 23: WO 2014/021908
Patent Document 24: WO 2013/081794
Patent Document 25: WO 2013/043785
Patent Document 26: WO 2013/043787

Non-Patent Documents

Non-Patent Document 1: A. N. Nesmeyanov et al., Tetrahedron, 1962, 17, 61
Non-Patent Document 2: M. S. Wrighton et al., J. Organomet. Chem., 1977, 128, 345
Non-Patent Document 3: F. Kakiuchi et al., J. Organomet. Chem., 1993, 456, 45
Non-Patent Document 4: H. Nakazawa et al., J. Am. Chem. Soc., 2012, 134, 804
Non-Patent Document 5: H. Nakazawa et al., Organometallics, 2012, 31, 3825
Non-Patent Document 6: P. J. Chirik et al., Organometallics, 2012, 31, 4886
Non-Patent Document 7: P. J. Chirik et al., J. Am. Chem. Soc., 2004, 126, 13794
Non-Patent Document 8: P. J. Chirik et al., Science, 2012, 335, 567
Non-Patent Document 9: A. J. Chalk et al., J. Am. Chem. Soc., 1965, 87, 1133
Non-Patent Document 10: A. J. Chalk et al., J. Am. Chem. Soc., 1967, 89, 1640
Non-Patent Document 11: A. J. Chalk et al., J. Organomet. Chem., 1970, 21, 207

Non-Patent Document 12: B. A. Izmailov et al., J. Organomet. Chem., 1978, 149, 29

Non-Patent Document 13: N. Sonoda et al., J. Org. Chem., 1987, 52, 4864

Non-Patent Document 14: S. Murai et al., Chem. Lett., 2000, 14

Non-Patent Document 15: M. S. Wrighton et al., Inorg. Chem., 1980, 19, 3858

Non-Patent Document 16: B. E. Grant et al., J. Am. Chem. Soc., 1993, 115, 2151

Non-Patent Document 17: L. Deng et al., Angew. Chem. Int. Ed., 2013, 52, 10845

Non-Patent Document 18: M. Umeno et al., J. Organomet. Chem., 1973, 50, 297

Non-Patent Document 19: I. Kownacki et al., J. Organomet. Chem., 2000, 597, 175

Non-Patent Document 20: P. Valerga et al., Dalton Trans., 2007, 3000

Non-Patent Document 21: T. D. Tilley et al., Chem. Commun., 2012, 48, 7146

Non-Patent Document 22: P. Valerga et al., Organometallics, 2012, 31, 2175

Non-Patent Document 23: T. A. Nile et al., J. Organomet. Chem., 1977, 137, 293

Non-Patent Document 24: M. R. Buchmeiser et al., J. Organomet. Chem., 2005, 690, 4433

Non-Patent Document 25: X. Li et al., J. Organomet. Chem., 2011, 696, 2116

Non-Patent Document 26: S. P. Nolan et al., Dalton Trans., 2013, 42, 270

Non-Patent Document 27: J. M. Walters et al., J. Molecular Catalysis, 1985, 29, 201

Non-Patent Document 28: M. F. Lappert et al., J. Organomet. Chem., 1979, 172, 153

SUMMARY OF THE INVENTION

Problems to be Solved by the Invention

An object of the invention, which has been made under the above-mentioned circumstances, is to provide a hydrosilylation reaction catalyst which helps hydrosilylation reaction take place under mild conditions and is improved in handling and storage; and a method for preparing an addition compound by hydrosilylation reaction using the same.

Means for Solving the Problems

Making extensive investigations to attain the above objects, the inventors have found that a catalyst which is obtained using a specific metal compound as the catalyst precursor and an isocyanide compound as the ligand component exerts a high activity to hydrosilylation reaction and helps addition reaction take place under mild conditions. The invention is predicated on this finding.

The invention provides a catalyst and a method defined below.

1. A hydrosilylation reaction catalyst which is prepared from:

a metal salt compound having the formula (1):

$$M_a(L)_b(X)_c \quad (1)$$

wherein M is a transition metal selected from Groups 8, 9 and 10 in the Periodic Table, exclusive of platinum, X is a halogen atom, L is a monovalent organic group of at least one type selected from the formulae (3) to (5), a is an integer of 1 or 2, b is an integer of 0 to 6, c is an integer of 0 to 3, satisfying b+c=2 or 3 when a is 1, and b+c=4 to 6 when a is 2, $$—O—R^1 \quad (3)$$

$$—OCO—R^1 \quad (4)$$

$$—OSO_2—R^1 \quad (5)$$

wherein $R^1$ is each independently an optionally substituted, $C_1$-$C_{20}$ monovalent organic group which may be separated by at least one atom selected from oxygen, nitrogen, sulfur and phosphorus, or a monovalent organic group having the formula (6):

$$-(A)_p-R^2 \quad (6)$$

wherein A is an optionally substituted, $C_1$-$C_{20}$ divalent organic group which may be separated by at least one atom selected from oxygen, nitrogen, sulfur and phosphorus, p is an integer of 0 or 1, satisfying p=0 or 1 when L is a monovalent organic group having formula (3), and p=1 when L is a monovalent organic group having formula (4) or (5), $R^3$ is a group having the formula (7):

$$—\{Si(R^3)_2—R^4\}_s—Si(R^3)\{[(OSi(R^3)_2)]_f—R^3\}_e \quad (7)$$

wherein $R^3$ is each independently an optionally substituted, $C_1$-$C_{20}$ alkyl group, $C_1$-$C_{20}$ alkoxy group, $C_6$-$C_{20}$ aryl group or $C_7$-$C_{20}$ aralkyl group which may be separated by at least one atom selected from oxygen, nitrogen, sulfur and phosphorus, $R^4$ is a $C_1$-$C_{10}$ divalent hydrocarbon group, s is an integer of 0 or 1, d is an integer of 0 to 3, e is an integer of 0 to 3, satisfying d+e=3, and f is an integer of 1 to 300, and an isocyanide compound having the formula (2):

$$Y—(NC)_q \quad (2)$$

wherein Y is an optionally substituted, $C_1$-$C_{30}$ monovalent organic group which may be separated by at least one atom selected from oxygen, nitrogen, sulfur and phosphorus, and q is an integer of 1 to 3.

2. The hydrosilylation reaction catalyst of 1 wherein in formula (2), q is 1 and in formula (7), a is 0.

3. The hydrosilylation reaction catalyst of 1 or 2 which is prepared in a system where hydrosilylation reaction of a compound having an aliphatic unsaturated bond with a hydrosilane compound having a Si—H group or organohydropolysiloxane compound is carried out.

4. The hydrosilylation reaction catalyst of any one of 1 to 3 wherein M is Fe, Co or Ni, a is 1, b is 2, and c is 0.

5. The hydrosilylation reaction catalyst of any one of 1 to 3 wherein M is Rh, a is 2, b is 4, and c is 0.

6. The hydrosilylation reaction catalyst of any one of 1 to 3 wherein M is Ru, a is 2, b is 4, and c is 1.

7. The hydrosilylation reaction catalyst of any one of 1 to 6 wherein L is a monovalent organic group having formula (4).

8. The hydrosilylation reaction catalyst of 7 wherein $R^1$ is a $C_1$-$C_5$ alkyl group which may be substituted with halogen.

9. The hydrosilylation reaction catalyst of any one of 1 to 8 wherein the isocyanide compound having formula (2) is at least one compound selected from the group consisting of mesityl isocyanide, n-butyl isocyanide, t-butyl isocyanide, 1,1,3,3-tetramethylbutyl isocyanide, cyclohexyl isocyanide, 1-isocyanoadamantane, 4-tolyl isocyanide, 1,6-diisocyanohexane, and 1,8-diisocyanooctane.

10. A method for preparing an addition compound comprising the step of carrying out hydrosilylation reaction of a compound having an aliphatic unsaturated bond with a hydrosilane compound having a Si—H group or organohydropolysiloxane compound in the presence of the hydrosilylation reaction catalyst of any one of 1 to 9.

11. The method for preparing an addition compound of 10 wherein the compound having an aliphatic unsaturated bond is an organopolysiloxane having an alkenyl group.

Advantageous Effects of the Invention

The metal compound from which the hydrosilylation reaction catalyst of the invention is prepared is readily available as a commercial product or synthesized by a well-known method. Also the metal compound is quite easy to handle without a need for storage at a low temperature or in an inert gas atmosphere or for weighing or handling in a glove box, and has the advantage that it maintains high reactivity even after long-term exposure to air.

On the other hand, the isocyanide compound serving as the ligand component may also be stored at room temperature and eliminates a need for a special equipment for handling.

Also, the inventive catalyst has advantages including high storage stability, ease of handling, and high reactivity since it is free of such a ligand as carbonyl, $\eta^6$-diene, $\eta^5$-cyclopentadienyl, $\eta^6$-arene or $\eta^6$-triene group.

In order to use a metal compound to generate a reactive species, generally a reducing agent capable of reducing a high valence metal species in a system must be added. According to the invention, the desired addition reaction by hydrosilylation takes place without a need to separately add a reducing agent because the substrate, hydrosilane itself is utilized as the reducing agent.

The catalyst prepared from the metal compound and isocyanide compound may be used after isolation as a metal complex compound or it may be prepared in situ in a hydrosilylation reaction system and used without isolation.

If hydrosilylation reaction between a compound containing an aliphatic unsaturated group and a silane having a Si—H group or polysiloxane is carried out in the presence of the catalyst prepared from the metal compound and isocyanide compound, addition reaction is possible under such conditions as room temperature to 100° C. In particular, addition reaction with industrially useful polysiloxanes, trialkoxysilanes and dialkoxysilanes takes place effectively.

Although the cited documents describe that in the relevant reaction, addition reaction to an unsaturated group and reaction to produce an unsaturated group-containing compound by dehydrogenation silylation reaction often take place at the same time, the use of the inventive catalyst ensures selective progress of addition reaction to an unsaturated group.

In addition, with respect to the reaction with an internal olefin which is difficult with the prior art catalysts, an addition reaction product with the unsaturated group migrating to the terminus is obtainable according to the invention. The invention is thus quite useful in the silicone industry.

BRIEF DESCRIPTION OF THE DIAGRAMS

EMBODIMENT FOR CARRYING OUT THE INVENTION

Figure 1:
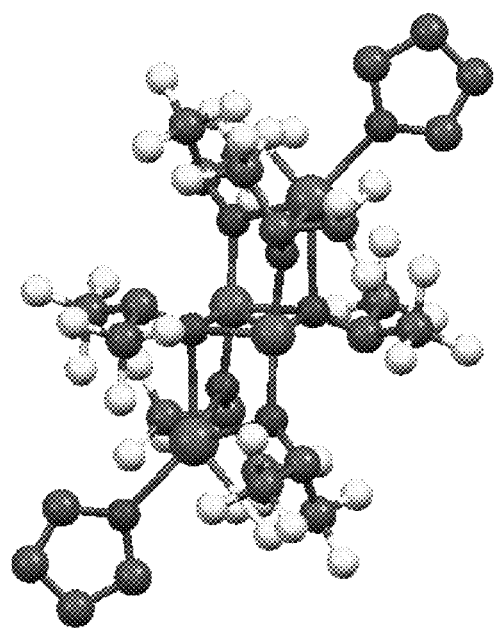
FIG. 1 is a model showing the results of x-ray crystallographic analysis on iron complex A obtained in Synthesis Example 7.

Below the invention is described in more detail.

The invention provides a hydrosilylation reaction catalyst which is prepared from a metal compound having the formula (1) serving as a catalyst precursor and an isocyanide compound having the formula (2) serving as a ligand.

$$M_a(L)_b(X)_c \qquad (1)$$

$$Y-(NC)_q \qquad (2)$$

In formula (1), M is a transition metal selected from Groups 8, 9 and 10 in the Periodic Table, exclusive of platinum, preferably Fe, Co, Ni, Ru, Rh, Pd, Os, and Ir. With the availability and cost of the metal salt, catalytic activity and other factors taken into account, Fe, Co, Ni, Ru, Rh, Os, and Ir are more preferred, and Fe, Co, Ru, Ni, and Rh are even more preferred.

X is a halogen atom, for example, fluorine, chlorine, bromine, and iodine atoms. Chlorine and bromine atoms are preferred, with chlorine atoms being more preferred.

L is a monovalent organic group to bond with the transition metal M via oxygen, specifically a monovalent organic group of at least one type selected from the formulae (3) to (5), preferably a monovalent organic group of formula (4).

$$-O-R^1 \qquad (3)$$

$$OCO-R^1 \qquad (4)$$

$$OSO_2-R^1 \qquad (5)$$

In formulae (3) to (5), $R^1$ is each independently a $C_1$-$C_{30}$ monovalent organic group or a monovalent organic group having the formula (6).

$$-(A)_p-R^2 \qquad (6)$$

The $C_1$-$C_{30}$ monovalent organic groups are preferably $C_1$-$C_{30}$ monovalent hydrocarbon groups, but not limited thereto.

Suitable monovalent hydrocarbon groups include alkyl, alkenyl, alkynyl, aryl and aralkyl groups.

The alkyl groups may be straight, branched or cyclic ones, preferably $C_1$-$C_{20}$, more preferably $C_1$-$C_{10}$ alkyl groups. Examples include straight or branched alkyl groups such as methyl, ethyl, n-propyl, isopropyl, n-butyl, isobutyl, s-butyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-eicosanyl; and cycloalkyl groups such as cyclopropyl, cyclobutyl, cyclopentyl, cyclohexyl, cycloheptyl, cyclooctyl, cyclononyl, norbornyl, and adamantyl.

The alkenyl groups are preferably $C_2$-$C_{20}$ alkenyl groups. Examples include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pentenyl, n-1-decenyl, and n-1-eicosenyl.

The alkynyl groups are preferably $C_2$-$C_{29}$ alkynyl groups. Examples include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecenyl, and n-1-eicosanyl.

The aryl groups are preferably $C_5$-$C_{30}$, more preferably $C_6$-$C_{20}$ aryl groups. Examples include phenyl, 1-naphthyl, 2-naphthyl, anthryl, phenanthryl, o-biphenylyl, m-biphenylyl, and p-biphenylyl.

The aralkyl groups are preferably $C_7$-$C_{30}$, more preferably $C_7$-$C_{20}$ aralkyl groups. Examples include benzyl, phenylethyl, phenylpropyl, naphthylmethyl, naphthylethyl, and naphthylpropyl.

In these groups, one or more atoms selected from oxygen, nitrogen, sulfur and phosphorus may intervene as long as the activity of the inventive hydrosilylation reaction catalyst is not impaired.

The $C_1$-$C_{30}$ monovalent organic group may have a substituent or substituents of the same or different type at arbitrary positions. Examples of the substituent include halogen atoms such as fluorine and chlorine, alkoxy groups such as methoxy, ethoxy and propoxy, and amino groups such as dialkylamino groups.

In formula (6), A is an optionally substituted, $C_1$-$C_{30}$ divalent organic group which may be separated by at least one atom selected from oxygen, nitrogen, sulfur and phosphorus, p is an integer of 0 or 1, satisfying p=0 or 1 when L is a monovalent organic group having formula (3), and p=1 when L is a monovalent organic group having formula (4) or (5).

The $C_1$-$C_{30}$ divalent organic groups are preferably $C_1$-$C_{30}$ divalent hydrocarbon groups, but not limited thereto.

Suitable divalent hydrocarbon groups include alkylene, arylene and aralkylene groups.

The alkylene groups may be straight, branched or cyclic ones, preferably $C_1$-$C_{20}$, more preferably $C_1$-$C_{10}$ alkylene groups. Examples include straight or branched alkylene groups such as methylene, ethylene, propylene, trimethylene, n-butylene, isobutylene, s-butylene, n-octylene, 2-ethylhexylene, n-decylene, n-undecylene, n-dodecylene, n-tridecylene, n-tetradecylene, n-pentadecylene, n-hexadecylene, n-heptadecylene, n-octadecylene, n-nonadecylene, and n-eicosanylene; and cycloalkylene groups such as 1,4-cyclohexylene.

The arylene groups are preferably $C_6$-$C_{30}$, more preferably $C_6$-$C_{30}$ arylene groups. Examples include o-phenylene, m-phenylene, p-phenylene 1,2-naphthylene, 1,8-naphthylene, 2,3-naphthylene, and 4,4'-biphenylene.

The aralkylene groups are preferably $C_7$-$C_{30}$, more preferably $C_7$-$C_{20}$ aralkylene groups. Examples include —(CH$_2$)$_k$—Ar— wherein Ar is a $C_6$-$C_{29}$ arylene group and k is an integer of 1 to 10, —Ar—(CH$_2$)$_k$— wherein Ar and k are as defined above, and —(CH$_2$)$_k$—Ar—(CH$_2$)$_k$— wherein Ar is as defined above and k is each independently as defined above.

$R^2$ is a silyl or polyorganosiloxane group having the formula (7).

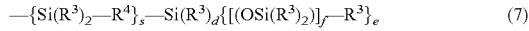
$$-\{Si(R^3)_2-R^4\}_s-Si(R^3)_d\{[(OSi(R^3)_2)]_f-R^3\}_e \quad (7)$$

In formula (7), $R^3$ is an optionally substituted, $C_1$-$C_{30}$ alkyl group, alkoxy group, aryl group or aralkyl group which may be separated by at least one atom selected from oxygen, nitrogen, sulfur and phosphorus, and $R^4$ is a $C_1$-$C_{10}$ divalent hydrocarbon group.

The $C_1$-$C_{20}$ alkoxy groups are preferably $C_1$-$C_{10}$ alkoxy groups. Examples include methoxy, ethoxy, n-propoxy, i-propoxy, n-butoxy, i-butoxy, s-butoxy, t-butoxy, n-pentoxy, n-hexoxy, n-heptyloxy, n-octyloxy, n-nonyloxy, and n-decyloxy.

Suitable alkyl, aryl and aralkyl groups are as exemplified above for $R^1$.

Examples of the substituent include halogen atoms such as fluorine and chlorine, alkoxy groups such as methoxy, ethoxy and propoxy, and amino groups such as dialkylamino groups.

Examples of the $C_1$-$C_{10}$ divalent hydrocarbon group represented by $R^4$ include alkylene groups such as ethylene and propylene, preferably ethylene.

The subscript a is an integer of 0 or 1, d is an integer of 0 to 3, e is an integer of 0 to 3, satisfying d+e=3, and f is an integer of 1 to 300. Preferred is a silyl or polyorganosiloxane group having the formula (7') corresponding to formula (7) wherein s=0.

$$-Si(R^3)_d\{[(OSi(R^3)_2)]_f-R^3\}_e \quad (7')$$

Examples of the silyl or polyorganosiloxane group having formula (7) include, but are not limited to, trimethylsilyl, triethylsilyl, phenyldimethylsilyl, trimethoxysilyl, triethoxysilyl, pentamethyldisiloxy, bistrimethylsiloxymethylsilyl, tristrimethylsiloxysilyl, polydimethylsiloxy groups of the formula:
—Si(Me)$_2$$\{$(OSi(Me)$_2$$\}_{f-1}$-OSiMe$_3$ wherein f is as defined above, and polydimethylsiloxy groups of the formula:
—Si(Me)$_2$$\{$OSi(Me)$_2$$\}_{f-1}$-OSiMe$_2$nBu wherein f is as defined above.

Besides the groups of formula (7), $R^2$ may be a siloxane group of dendrimer type which is highly branched via silethylene groups.

Of the foregoing, $R^1$ is preferably an optionally halo-substituted, $C_1$-$C_{30}$ monovalent hydrocarbon group, more preferably an optionally halo-substituted, $C_1$-$C_{10}$ alkyl group, and even more preferably an optionally halo-substituted, $C_1$-$C_5$ alkyl group.

In formula (1), a is 1 or 2, b is an integer of 0 to 6, and c is an integer of 0 to 3, which are selected in accordance with the valence number of metal M so as to satisfy b+c=2 or 3 when a is 1, and b+c=4 to 6 when a is 2.

Specifically, when M in formula (1) is Fe, Co or Ni, preferably a is 1, b is 2 or 0, and c is 0, 2 or 3; more preferably a is 1, b is 2, and c is 0.

When M in formula (1) is Rh, preferably a is 2, b is 4, and c is 0.

When M in formula (1) is Ru, preferably a is 2, b is 4, and c is 1.

Examples of the metal compound which may be preferably used herein as the catalyst precursor include, but are not limited to, iron compounds such as iron(II) acetate, iron(II) pivalate, iron(II) trifluoroacetate (tetrahydrofuran complex, referred to as THF hereinafter), and iron-oxygen bond-bearing iron complexes prepared from [Fe(mesityl)(μ-mesityl)]$_2$ and alcohols, carboxylic acids or siloxane-containing carboxylates; cobalt compounds such as cobalt(II) acetate, cobalt(II) chloride, cobalt(II) bromide, cobalt(II) isopropoxide, cobalt(II) pivalate, and cobalt(II) trifluoroacetate (THF); nickel compounds such as nickel(II) acetate and nickel(II) pivalate; ruthenium compounds such as Ru$_2$(μ-OAc)$_4$Cl; and rhodium compounds such as rhodium(II) acetate dimer.

It is noted that these metal salts may be obtained as commercial products or synthesized by the methods described in the literature (J. Cluster Sci., 2005, 16, 331; Inorganic Chemistry, 2007, 46, 3378; Organometallics, 1993, 12, 2414; Russ. Chem. Bull., 1999, 48, 1751; J. Inorg. Nucl. Chem., 1966, 28, 2285, etc.).

In formula (2), Y is an optionally substituted, $C_1$-$C_{30}$ monovalent organic group which may be separated by at least one atom selected from oxygen, nitrogen, sulfur and phosphorus, and q is an integer of 1 to 3, preferably 1.

The $C_1$-$C_{20}$ monovalent organic groups are preferably $C_1$-$C_{30}$ monovalent hydrocarbon groups, but not limited thereto.

Suitable monovalent hydrocarbon groups include alkyl, alkenyl, alkynyl, aryl and aralkyl groups. Examples of the alkyl, alkenyl, alkynyl, aryl and aralkyl groups are as exemplified above for $R^1$.

Examples of the substituent on Y include halogen atoms such as fluorine, chlorine, bromine and iodine, alkoxy groups such as methoxy, ethoxy and propoxy, and amino groups such as dialkylamino groups.

Examples of the isocyanide compound which may be preferably used herein as the ligand include, but are not limited to, alkyl isocyanides such as methyl isocyanide, ethyl isocyanide, n-propyl isocyanide, cyclopropyl isocyanide, n-butyl isocyanide, isobutyl isocyanide, sec-butyl isocyanide, t-butyl isocyanide, n-pentyl isocyanide, isopentyl isocyanide, neopentyl isocyanide, 1,1,3,3-tetramethylbutyl isocyanide, n-hexyl isocyanide, cyclohexyl isocyanide, cycloheptyl isocyanide, 1,1-dimethylhexyl isocyanide, 1-adamantyl isocyanide, and 2-adamantyl isocyanide; aryl isocyanides such as phenyl isocyanide, 2-methylphenyl isocyanide, 4-methylphenyl isocyanide (4-tolyl isocyanide), 2,4-dimethylphenyl isocyanide, 2,5-dimethylphenyl isocyanide, 2,6-dimethylphenyl isocyanide, 2,4,6-trimethylphenyl isocyanide (mesityl isocyanide), 2,4,6-tri-t-butylphenyl isocyanide, 2,6-diisopropylphenyl isocyanide, 1-naphthyl isocyanide, 2-naphthyl isocyanide, and 2-methyl-1-naphthyl isocyanide; and aralkyl isocyanides such as benzyl isocyanide and phenylethyl isocyanide.

Examples of the diisocyanide compound include 1,2-diisocyanoethane, 1,3-diisocyanopropane, 1,4-diisocyanobutane, 1,5-diisocyanopentane, 1,6-diisocyanohexane, 1,8-diisocyanooctane, 1,12-diisocyanododecane, 1,2-diisocyanocyclohexane, 1,3-diisocyanocyclohexane, 1,4-diisocyanocyclohexane, 1,3-diisocyano-2, 2-dimethylpropane, 2,5-diisocyano-2,5-dimethylhexane, 1,2-bis(diisocyanoethoxy)ethane, 1,2-diisocyanobenzene, 1,3-diisocyanobenzene, 1,4-diisocyanobenzene, 1,1'-methylenebis(4-isocyanobenzene), 1,1'-oxybis(4-isocyanobenzene), 3-(isocyanomethyl)benzyl isocyanide, 1,2-bis(2-isocyanophenoxy)ethane, bis(2-isocyanophenyl)phenyl phosphonate, bis(2-isocyanophenyl) isophthalate, and bis(2-isocyanophenyl) succinate.

Examples of the triisocyanide compound include 1,3-diisocyano-2-(isocyanomethyl)-2-methylpropane, 1,5-diisocyano-3-(2-isocyanoethyl)pentane, 1,7-diisocyano-4-(3-isocyanopropyl)heptane, and 3-isocyano-N,N'-bis(3-isocyanopropyl)propane-1-amine.

These isocyanide compounds may be synthesized, for example, from an amine compound corresponding to the isocyanide by the method involving formylation and dehydration reactions, or from benzoxazole by the method described in Organometallics, 2013, 21, 7153-7162.

In preparing the inventive hydrosilylation reaction catalyst, the amounts of the metal compound and the isocyanide compound used are not particularly limited. Preferably the isocyanide compound is used in an amount of about 0.5 to 10 equivalents, more preferably 1 to 6 equivalents, and even more preferably 2 to 4 equivalents per equivalent of the metal compound.

When hydrosilylation reaction is carried out in the presence of the inventive hydrosilylation reaction catalyst, the amount of the catalyst used is not particularly limited. In order that the reaction take place under mild conditions of the order of room temperature to 100° C. to form the desired product in high yields, the catalyst is preferably used in an amount of at least 0.01 mol %, more preferably at least 0.05 mol % of metal compound per mole of the substrate, aliphatic unsaturated bond-containing compound.

Although no upper limit is imposed on the amount of metal compound used, the upper limit is preferably about 10 mol %, more preferably 5 mol % per mole of the substrate, as viewed from the economic standpoint.

Notably, a well-known two-electron donative ligand may be used in combination with the inventive hydrosilylation reaction catalyst as long as the activity of the catalyst is not impaired. Although the two-electron donative ligand is not particularly limited, ligands other than carbonyl are preferred, for example, ammonia molecules, ether compounds, amine compounds, phosphine compounds, phosphite compounds, and sulfide compounds.

In a preferred embodiment, the inventive hydrosilylation reaction catalyst is prepared from the metal compound and the isocyanide compound in a system where hydrosilylation reaction of a compound having an aliphatic unsaturated bond with a hydrosilane compound having a Si—H group or organohydropolysiloxane compound is carried out.

In this embodiment, once the catalyst is prepared from the metal compound and the isocyanide compound, the compound having an aliphatic unsaturated bond and the hydrosilane compound having a Si—H group or organohydropolysiloxane compound may be added thereto, or separate sets of some components may be fed, or all components may be fed at a time.

Although the reaction conditions for the metal compound and the isocyanide compound are not particularly limited, generally the reaction temperature is about 10 to about 100° C., preferably 30 to 80° C. and the reaction time is about 1 to about 48 hours.

Although an organic solvent may be used during preparation of the catalyst and hydrosilylation reaction, the invention favors a solventless or neat system.

The organic solvent, if used, may be of any type as long as the reaction is not affected. Examples include aliphatic hydrocarbons such as pentane, hexane, heptane, octane, and cyclohexane, ethers such as diethyl ether, diisopropyl ether, dibutyl ether, cyclopentyl methyl ether, tetrahydrofuran and 1,4-dioxane; and aromatic hydrocarbons such as benzene, toluene, xylene, and mesitylene.

In conducting hydrosilylation reaction using the inventive hydrosilylation reaction catalyst, as long as a compound having an aliphatic unsaturated bond such as an olefin, silane or organopolysiloxane compound having an aliphatic unsaturated bond and a silane or organopolysiloxane compound having a Si—H bond are used in combination, no limit is imposed on the structure of the respective compounds.

The hydrosilylation reaction using the inventive hydrosilylation reaction catalyst is applicable to all applications which are industrially implemented using prior art platinum catalysts, including silane coupling agents obtained from an olefin compound having an aliphatic unsaturated bond and a silane compound having a Si—H bond, and modified silicone oils obtained from an olefin compound having an aliphatic unsaturated bond and an organopolysiloxane having a Si—H bond, as well as silicone cured products obtained from an organopolysiloxane compound having an aliphatic unsaturated bond and an organopolysiloxane having a Si—H bond.

EXAMPLES

Synthesis Examples, Examples and Comparative Examples are given below by way of illustration and not by way of limitation.

All solvents were deoxygenated and dehydrated by well-known methods before they were used in the preparation of metal compounds.

The metal compounds obtained were stored in a nitrogen gas atmosphere at 25° C. before they were used in reaction.

Hydrosilylation reaction and solvent purification of alkenes were always carried out in an inert gas atmosphere. The solvents and other ingredients were purified, dried and deoxygenated by well-known methods before they were used in various reactions.

Analyses of $^1$H, $^{13}$C and $^{15}$F-NMR spectroscopy were performed by JNM-ECA 600 and JNM-LA 400 of JEOL Ltd., IR spectroscopy by FT/IR-550 of JASCO Corp., elemental analysis by 2400II/CHN of Perkin Elmer, x-ray crystallography analysis by VariMax (MoK α-ray 0.71069 angstrom) of Rigaku Corp.

It is understood that hydrogen atoms are omitted from the chemical structural formula, shown below, according to the conventional expression. OAc stands for an acetate anion, and iPr for isopropyl.

(1) Synthesis of Metal Compounds

[Synthesis Example 1] Synthesis of Iron Pivalate

With reference to J. Cluster Sci., 2005, 16, 331, the compound was synthesized by the following procedure.

A 50 mL two-neck recovery flask equipped with a reflux tube was charged with 0.86 g (15.4 mmol) of reduced iron and 3.50 g (34.3 mmol) of pivalic acid, which were stirred at 160° C. for 12 hours. On this occasion, the reaction solution turned from colorless clear to green. Further 2.50 g (24.5 mmol) of pivalic acid was added to the solution, which was stirred at 160° C. for 19 hours. Thereafter, the reaction solution was filtered, and the filtrate was combined with the recovered supernatant and dried in vacuum at 80° C. The resulting solid was washed with hexane, obtaining a green solid (2.66 g, yield 67%).

FT-IR (KBr) ν:
2963, 2930, 2868, 1583, 1523, 1485, 1457, 1427, 1379, 1362, 1229, 1031, 938, 900, 790, 608, 576, 457 cm$^{-1}$

[Synthesis Example 2] Synthesis of Iron Trifluoroacetate (THF)

With reference to Inorganic Chemistry, 2007, 46, 3378, the compound was synthesized by the following procedure.

A 20 mL Schlenk flask was charged with 1.00 g (5.7 mmol) of iron acetate, 30 mL of THF, and 1.0 mL (13.1 mmol) of trifluoroacetic acid, which were stirred at 25° C. for 2 hours. On this occasion, the reaction solution turned to a dark red solution as initially suspended brown iron acetate gradually dissolved. The reaction product was dried in vacuum, dissolved in THF again, and purified by recrystallization from pentane, obtaining a white solid (0.29 mg). The yield was 15% provided that coordinated THF was one molecule.

FT-IR (KBr) ν:
3160, 3112, 2992, 2906, 1698, 1666, 1531, 1463, 1410, 1204, 1145, 1039, 916, 881, 845, 795, 723, 688, 612, 524 cm$^{-1}$

[Synthesis Example 3] Preparation of Iron Precursor Having Iron-Oxygen Bond Using [(Fe(Mesityl)(μ-Mesityl)]$_2$ With reference to Organometallics, 1993, 12, 2414, the compound was synthesized by the following procedure.

A 50 mL two-neck recovery flask was charged with 1.08 g (44.3 mmol) of magnesium ribbon and 35 mL of THF, after which 8.49 g (42.6 mmol) of bromomesitylene was slowly added dropwise. It was confirmed that exotherm ceased at the end of dropwise addition, after which the reaction solution was stirred at 60° C. for 3 hours. The solution was filtered through a glass filter, obtaining a THF solution of mesitylmagnesium bromide Grignard reagent.

A 100 mL Schlenk flask was charged with 2.63 g (20.7 mmol) of FeCl$_2$, 30 mL of THF, and 10 mL of 1,4-dioxane and cooled down to −78° C. The THF solution of mesitylmagnesium bromide Grignard reagent was slowly added to the flask, followed by stirring at 25° C. for 2 hours. On this occasion, the reaction solution turned from a brown suspension to a red suspension. Thereafter, the precipitated solid was separated by centrifugation and dried in vacuum. The resulting red solid was dissolved in diethyl ether, after which the solid was separated again by centrifugation and recrystallized at −30° C., obtaining a crystal (4.36 g, yield 72%). The crystal was identified by $^1$H-NMR analysis in C$_6$D$_6$.

$^1$H-NMR (600 MHz, C$_6$D$_6$) δ: 23.68 (s, 2H), 23.17 (s, 2H), 21.44 (s, 3H), 17.94 (s, 3H), 10.19 (s, 6H), −6.66 (s, 6H)

In a 20 mL Schlenk flask, 3 mg (0.01 mmol) or 9 mg (0.015 mmol) of the thus obtained [(Fe(mesityl)(μ-mesityl)]$_2$ was dissolved in 1 mL of THF. To the solution, a 2-fold equivalent amount, 0.02 mmol or 0.06 mmol of a carboxylic acid or alcohol (abbreviated as ROH, hereinafter) as shown in Table 2 was added, followed by stirring at 25° C. for 30 minutes. This was followed by vacuum drying, obtaining an iron precursor having an iron-oxygen bond (Fe(OR)$_2$).

[Synthesis Example 4] Synthesis of Cobalt Pivalate

With reference to Russ. Chem. Bull., 1999, 48, 1751, the compound was synthesized by the following procedure.

A 50 mL two-neck recovery flask equipped with a reflux tube was charged with 1.15 g (6.5 mmol) of cobalt acetate, 1.55 g (15.2 mmol) of pivalic acid, and 0.5 mL (2.5 mmol) of pivalic anhydride, which were stirred at 160° C. for 1 hour. On this occasion, the reaction solution turned from thin purple to purple. Thereafter, the reaction solution was vacuum dried at 80° C. The resulting solid was washed with pentane and diethyl ether and dried, obtaining a purple solid (1.15 g, yield 68%).

FT-IR (KBr) ν:
2963, 2929, 2868, 1599, 1524, 1485, 1457, 1420, 1379, 1363, 1229, 1032, 938, 900, 792, 613, 585, 460 cm$^{-1}$

[Synthesis Example 5] Synthesis of Cobalt Trifluoroacetate (THF)

With reference to Russ. J. Inorg. Chem., 1993, 38, 571, the compound was synthesized by the following procedure.

A 30 mL two-neck recovery flask equipped with a reflux tube was charged with 1.05 g (8.8 mmol) of cobalt carbonate, 1.3 mL (17.3 mmol) of trifluoroacetic acid, and 1.2 mL (8.8 mmol) of trifluoroacetic anhydride, which were stirred at 80° C. for 6 hours. On this occasion, the reaction solution turned from thin purple to dark purple. The reaction solution was cooled, once dried in vacuum, and dissolved in THF.

The solid left undissolved was separated by centrifugation. The resulting purple liquid was concentrated under reduced pressure and recrystallized from pentane, obtaining a purple crystal (0.80 g). The yield was 26% provided that coordinated THF was one molecule.
FT-IR (KBr) ν:
3133, 2991, 2900, 1722, 1584, 1460, 1412, 1205, 1144, 1037, 922, 882, 839, 793, 719, 676, 618 cm$^{-1}$

[Synthesis Example 6] Synthesis of Ru$_3$(μ-OAc)$_4$Cl

With reference to J. Inorg. Nucl. Chem., 1966, 28, 2285, the compound was synthesized by the following procedure.
A 200 mL two-neck recovery flask was charged with 1.09 g (4.18 mmol) of RuCl$_3$ trihydrate, 35 mL of glacial acetic acid, and 7 mL of acetic anhydride, which were stirred at 145° C. for 2 hours. The reaction solution was cooled, once filtered, and stirred again at 145° C. for 6 hours. Then the reaction product was crystallized at −30° C., and washed with glacial acetic acid, methanol and diethyl ether, obtaining a reddish brown solid (61 mg, yield 6%).
FT-IR (KBr) ν:
3023, 2991, 2934, 1643, 1444, 1401, 1356, 1041, 1015, 944, 691, 625, 606 cm$^{-1}$

[Synthesis Example 7] Synthesis of Iron Complex A

A 100 mL two-neck recovery flask with a stirrer was charged with 550 mg (12.6 mmol) of NaH (55%) in paraffin and 20 mL of diethyl ether, and cooled down to 0° C. To the flask, 2.50 mL (24.1 mmol) of 1,1,1,3,3,3-hexafluoroisopropanol was slowly added dropwise, followed by stirring at 25° C. for 1 hour. Thereafter, the reaction product was dried in vacuum and washed 3 times with hexane, obtaining 2.45 g of sodium 1,1,1,3,3,3-hexafluoroisopropoxide (abbreviated as NaHFIP, hereinafter).
In a nitrogen-blanketed glove box, 0.10 g (0.79 mmol) of FeCl$_2$ and 5 mL of toluene were added to a screw-top vial with a stirrer. A solution of 0.33 g (1.71 mmol) of NaHFIP in 1 mL of THF was added dropwise to the vial, followed by stirring at 25° C. for 1 week. Thereafter, the solid was removed by centrifugation, and the reaction product was recrystallized at −30° C., obtaining iron complex A (78 mg, yield 15%). The result of x-ray crystallography analysis on iron complex A is depicted in FIG. 1.
(2) Hydrosilylation of Styrene with 1,1,3,3,3-Pentamethyldisiloxane Using Iron Compound and Isocyanide Ligand

[Chemical Formula 1]

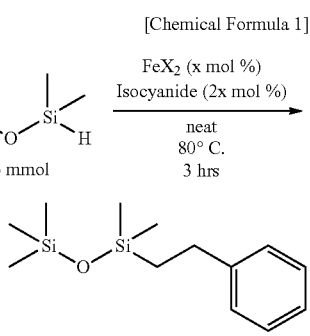

[Example 1] Hydrosilylation Reaction Using Iron Acetate and 1-Isocyanoadamantane A 20 mL Schlenk flask was charged with 5 mg (0.03 mmol) of iron acetate (commercial product) as a catalyst precursor, 10 mg (0.06 mmol) of 1-isocyanoadamantane as a ligand, and 254 μL (1.3 mmol) of 1,1,3,3,3-pentamethyldisiloxane, which were stirred at 80° C. for 1 hour to activate the catalyst.
After cooling, 115 μL (1.0 mmol) of styrene as a substrate was added, followed again by stirring at 80° C. for 3 hours. After cooling, 1.0 mmol of anisole as an internal standard was added to the reaction solution and stirred. A minute amount of the solution was dissolved in deuteronchloroform, passed through an alumina column to remove the catalyst, and analyzed by $^1$H-NMR spectroscopy to determine the structure and yield of the product. (It is noted that in the following Examples, a test sample was prepared according to the same procedure and analyzed by $^1$H-NMR spectroscopy.)
As a result, it was confirmed that the signal assigned to the ethylene site of styrene as the reactant disappeared completely. Instead, a multiplet at 0.89 ppm indicative of the signal assigned to proton on silicon-adjoining carbon in the desired product, 1,1,3,3,3-pentamethyl-3-phenethyldisiloxane was observed. The results are shown in Table 1.
$^1$H-NMR (396 MHz, CDCl$_3$) δ: 0.07 (s, 6H), 0.09 (s, 9H), 0.86-0.92 (m, 2H), 2.61-2.68 (m, 2H), 7.13-7.33 (m, 5H)

[Example 2] Hydrosilylation Reaction Using Iron Pivalate and t-Butyl Isocyanide

In a nitrogen-blanketed glove box, 8 mg (0.03 mmol) of iron pivalate in Synthesis Example 1, 5 mg (0.06 mmol) of t-butyl isocyanide, 254 μL (1.3 mmol) of 1,1,3,3,3-pentamethyldisiloxane, and 115 μL (1.0 mmol) of styrene were added to a screw-top vial with a stirrer. The vial was closed, after which the contents were stirred at 80° C. for 3 hours. After cooling, analysis was made by $^1$H-NMR spectroscopy to determine the structure and yield of the product. As a result, it was confirmed that the signal assigned to the reactant disappeared completely. Instead, a multiplet at 0.89 ppm indicative of the signal assigned to proton on silicon-adjoining carbon in the desired product was observed, from which a yield was computed. The results are shown in Table 1.

[Example 3] Hydrosilylation Reaction Using Iron Trifluoroacetate and t-Butyl Isocyanide Reaction was carried out according to the same procedure as in Example 2 aside from using 12 mg (0.03 mmol) of iron trifluoroacetate in Synthesis Example 2 instead of iron pivalate. As a result, it was confirmed that the signal assigned to the ethylene site of styrene as the reactant disappeared completely. Instead, a multiplet at 0.89 ppm indicative of the signal assigned to proton on silicon-adjoining carbon in the desired product was observed, from which a yield was computed. The results are shown in Table 1.

[Example 4] Hydrosilylation Reaction Using Iron Complex A and t-Butyl Isocyanide Reaction was carried out according to the same procedure as in Example 2 aside from using 20 mg (0.03 mmol) of iron complex A in Synthesis Example 7 instead of iron pivalate. As a result, it was confirmed that the signal assigned to the reactant disappeared completely. Instead, a multiplet at 0.89 ppm indicative of the signal assigned to the desired product was observed, from which a yield was computed. The results are shown in Table 1.

[Example 5] Hydrosilylation Reaction Using Iron Complex B

In a 20 mL Schlenk flask, 205 mg (0.79 mmol) of iron pivalate in Synthesis Example 1 was dissolved in 5 mL of THF. To the solution, 0.36 mL (3.22 mmol) of t-butyl isocyanide was added, followed by stirring at 25° C. for 30 minutes. The solution turned from green to orange color. This was followed by vacuum drying, obtaining 212 mg (yield 43%) of iron complex B as yellow powder.

FT-IR (KBr) ν:
2977, 2869, 2178 [ν (CNR)], 2151 [shoulder peak, ν (CNR)], 1613 [ν (COCtBu$_3$-κ$^2$)], 1565, 1550, 1536, 1484, 1462, 1423, 1373, 1326, 1207, 1044, 896, 808, 793, 607, 581, 572 cm$^{-1}$ $^1$H-NMR (600 MHz, CDCl$_3$) δ: −3.83 (br, 36H), 21.43 (br, 18H)

To a reactor, 18 mg (0.03 mmol) of iron complex B, 254 μL (1.3 mmol) of 1,1,3,3,3-pentamethyldisiloxane and 115 μL (1.0 mmol) of styrene were added. The reactor was closed, after which the contents were stirred at 80° C. for 3 hours. After cooling, analysis was made by $^1$H-NMR spectroscopy to determine the structure and yield of the product. As a result, it was confirmed that the signal assigned to the reactant disappeared completely. Instead, a multiplet at 0.89 ppm indicative of the signal assigned to proton on silicon-adjoining carbon in the desired product was observed, from which a yield was computed. The results are shown in Table 1.

[Example 6] Hydrosilylation Reaction Using Iron Complex C

Figure 2:
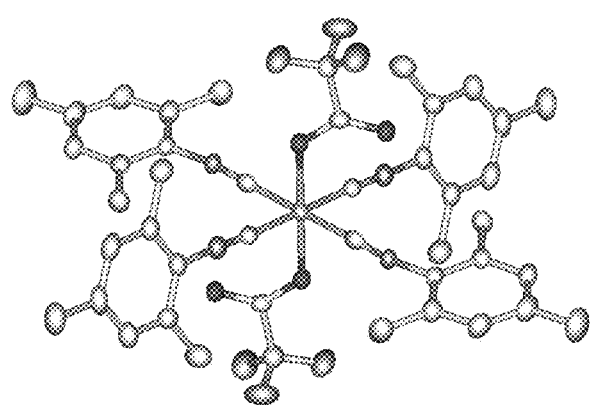
FIG. 2 is a model showing the results of x-ray crystallographic analysis on iron complex C obtained in Example 6.

In accordance with the procedure of Synthesis Example 3, 41 mg (0.07 mmol) of [Fe(mesityl)(μ-mesityl)]$_2$ was dissolved in 4 mL of THF. Then 21 μL (0.28 mmol) of trifluoroacetic acid was added to the solution, which was stirred at 25° C. for 30 minutes. Further, 43 mg (0.30 mmol) of mesityl isocyanide was added to the solution, which was stirred at 25° C. for 30 minutes. The solution turned from brown to orange color. This was followed by vacuum drying and recrystallization from a toluene/pentane solvent mixture, obtaining 9 mg (yield 14%) of iron complex C as red crystal. The result of x-ray crystallography analysis on the crystal is depicted in FIG. 2.

FT-IR (KBr) ν:
3083, 3025, 2979, 2953, 2920, 2859, 2149 [ν (CNAr)], 1684 [ν (COCF$_3$-κ$^1$)], 1606, 1581, 1475, 1449, 1404, 1384, 1309, 1194, 1136, 1035, 852, 791, 727, 714, 601, 548, 526 cm$^{-1}$ $^1$H-NMR (600 MHz, CDCl$_3$) δ: 1.90 (br, trans-cis), 2.34 (s, cis), 2.48 (s, cis), 2.54 (s, trans), 6.41 (s, cis), 6.42 (s, cis), 6.45 (s, trans)
trans:cis ratio=2.7:1

$^{15}$F-NMR (565 MHz, CDCl$_3$) δ: −74.2 (br), −73.5

To a reactor, 9 mg (0.01 mmol) of iron complex C, 254 μL (1.3 mmol) of 1,1,3,3,3-pentamethyldisiloxane and 115 μL (1.0 mmol) of styrene were added. The reactor was closed, after which the contents were stirred at 80° C. for 3 hours. After cooling, analysis was made by $^1$H-NMR spectroscopy to determine the structure and yield of the product. As a result, it was confirmed that the signal assigned to the reactant disappeared completely. Instead, a multiplet at 0.89 ppm indicative of the signal assigned to proton on silicon-adjoining carbon in the desired product was observed, from which a yield was computed. The results are shown in Table 1.

[Example 7] Hydrosilylation Reaction Using Iron Pivalate in Air Storage and 1-Isocyanoadamantane A screw-top vial with a stirrer was charged with 8 mg (0.03 mmol) of iron pivalate in Synthesis Example 1, which was exposed to air (25° C., 60% RH) for one day. Thereafter, 10 mg (0.06 mmol) of 1-isocyanoadamantane, 254 μL (1.3 mmol) of 1,1,3,3,3-pentamethyldisiloxane and 115 μL (1.0 mmol) of styrene were added. The vial was purged with nitrogen, after which the contents were stirred at 50° C. for 24 hours. After cooling, analysis was made by $^1$H-NMR spectroscopy to determine the structure and yield of the product. As a result, it was confirmed that the signal assigned to the reactant disappeared completely. Instead, a multiplet at 0.89 ppm indicative of the signal assigned to proton on silicon-adjoining carbon in the desired product was observed, from which a yield was computed. The results are shown in Table 1.

TABLE 1

| | FeX$_n$ | Isocyanide | Catalyst amount (mol %) | Conversion (%) | Yield (%) |
|---|---|---|---|---|---|
| Example 1 | iron acetate | 1-isocyanoadamantane | 5 | >99 | >99 |
| Example 2 | iron pivalate | t-butyl isocyanide | 3 | >99 | 75 |
| Example 3 | iron trifluoroacetate | t-butyl isocyanide | 3 | >99 | 68 |
| Example 4 | iron complex A | t-butyl isocyanide | 3 | >99 | 76 |
| Example 5 (iron complex B) | iron pivalate | t-butyl isocyanide | 3 | >99 | 80 |
| Example 6 (iron complex C) | iron trifluoroacetate | mesityl isocyanide | 1 | >99 | 48 |
| Example 7 | iron pivalate (1 day storage in air) | 1-isocyanoadamantane | 3 | >99 | >99 |

[Examples 8 to 15] Hydrosilylation Reaction Using Iron Complex Having Iron-Oxygen Bond and t-Butyl Isocyanide

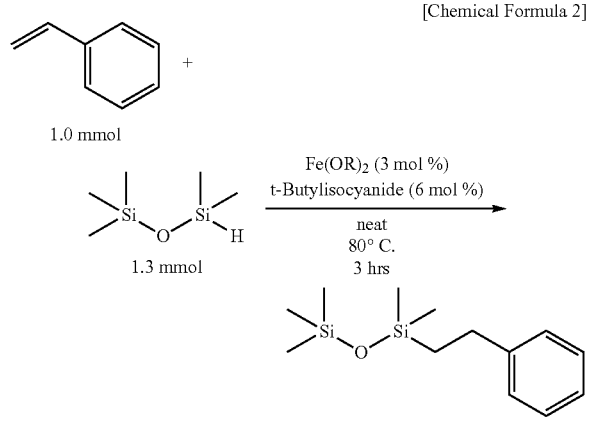

[Chemical Formula 2]

First, in accordance with the procedure of Synthesis Example 3, an iron catalyst precursor having an iron-oxygen bond $(Fe(OR)_2)$ was prepared from 9 mg (0.015 mmol) of $[Fe(mesityl)(\mu\text{-mesityl})]_2$ and 0.06 mmol of ROH shown in Table 2. To the reactor, 5 mg (0.06 mmol) of t-butyl isocyanide as a ligand, 254 µL (1.3 mmol) of 1,1,3,3,3-pentamethyldisiloxane and 115 µL (1.0 mmol) of styrene were added. The reactor was closed, after which the contents were stirred at 80° C. for 3 hours. After cooling, analysis was made by $^1$H-NMR spectroscopy to determine the structure and yield of the product. As a result, it was confirmed that the signal assigned to the reactant diminished or disappeared completely. Instead, a multiplet at 0.89 ppm indicative of the signal assigned to the desired product was observed, from which a yield was computed. The results are shown in Table 2.

TABLE 2

| ROH | Conversion (%) | Yield (%) |
| --- | --- | --- |
| Example 8 | 2,2,2-trifluoroethanol | >99 | 62 |
| Example 9 | 1,1,1,3,3,3-hexafluoroisopropanol | >99 | 72 |
| Example 10 | t-butanol | >99 | 66 |
| Example 11 | phenol | >99 | 60 |
| Example 12 | perfluorophenol | 25 | 17 |
| Example 13 | 3,5-bis (trifluoromethyl) phenol | 58 | 38 |
| Example 14 | pivalic acid | >99 | 67 |
| Example 15 | 2-thiophenecarboxylic acid | 98 | 64 |

[Examples 16, 17] Changes of Reaction Conditions from Examples 9, 14

Reaction was carried out according to the same procedure as in Example 9 or 14 aside from lowering the reaction temperature from 80° C. to 50° C. and extending the reaction time to 23 hours. As a result, it was confirmed that the signal assigned to the reactant disappeared completely. Instead, a multiplet at 0.89 ppm indicative of the signal assigned to the desired product was observed, from which a yield was computed. The results are shown in Table 3.

[Example 18] Reduction of Catalyst Amount from Example 16

In accordance with the procedure of Synthesis Example 3, an iron catalyst precursor having an iron-oxygen bond $(Fe(OR)_2)$ was prepared from 3 mg (0.005 mmol) of $[Fe(mesityl)(\mu\text{-mesityl})]_2$ and 16 mg (0.09 mmol) of 1,1,1,3,3,3-hexafluoroisopropanol. To the reactor, 2 mg (0.06 mmol) of t-butyl isocyanide, 1.94 g (13.0 mmol) of 1,1,3,3,3-pentamethyldisiloxane and 1.05 g (10.0 mmol) of styrene were added. The reactor was closed, after which the contents were stirred at 50° C. for 23 hours. After cooling, analysis was made by $^1$H-NMR spectroscopy to determine the structure and yield of the product. As a result, it was confirmed that the signal assigned to the reactant disappeared completely. Instead, a multiplet at 0.89 ppm indicative of the signal assigned to the desired product was observed, from which a yield was computed. The results are shown in Table 3.

TABLE 3

| | ROM | Fe(OR), (mol %) | Conversion (%) | Yield (%) |
| --- | --- | --- | --- | --- |
| Example 16 | 1,1,1,3,3,3-hexafluoroisopropanol | 3 | >99 | >99 |
| Example 17 | pivalic acid | 3 | >99 | >99 |
| Example 18 | 1,1,1,3,3,3-hexafluoroisopropanol | 0.1 | >99 | 97 |

[Example 19] Hydrosilylation Reaction Using Iron Complex Having Iron-Oxygen Bond and t-Butyl Isocyanide

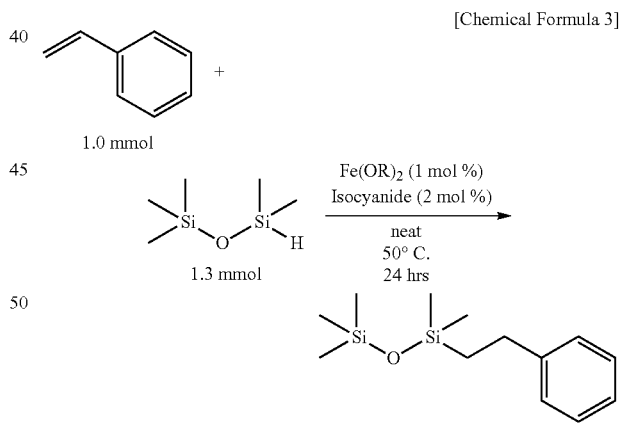

[Chemical Formula 3]

In accordance with the procedure of Synthesis Example 3, an iron precursor having an iron-oxygen bond $(Fe(OCOR)_2)$ was prepared from 3 mg (0.005 mmol) of $[Fe(mesityl)(\mu\text{-mesityl})]_2$ and 8 mg (0.02 mmol) of $(Me_3SiO)_2MeSi(CH_2)_{10}COOH$. To the reactor, 2 mg (0.02 mmol) of t-butyl isocyanide, 254 µL (1.3 mmol) of 1,1,3,3,3-pentamethyldisiloxane and 115 µL (1.0 mmol) of styrene were added. The contents were stirred at 50° C. for 24 hours. After cooling, analysis was made by $^1$H-NMR spectroscopy to determine the structure and yield of the product. The results are shown in Table 4.

[Example 20] Hydrosilylation Reaction Using Iron Complex Having Iron-Oxygen Bond and 1-Isocyanoadamantane Reaction was carried out according to the same procedure as in Example 19 aside from using 3 mg (0.02 mmol) of 1-isocyanoadamantane instead of t-butyl isocyanide. As a result, it was confirmed that the signal assigned to the reactant disappeared completely. Instead, a multiplet at 0.89 ppm indicative of the signal assigned to the desired product was observed, from which a yield was computed. The results are shown in Table 4.

Comparative Example 1

Reaction was carried out according to the same procedure as in Example 19 except that t-butyl isocyanide was omitted. Reaction did not take place. The results are shown in Table 4.

TABLE 4

|  | Isocyanide | Conversion (%) | Yield (%) |
|---|---|---|---|
| Example 19 | t-butyl isocyanide | 71 | 60 |
| Example 20 | 1-isocyanoadamantane | >99 | 98 |
| Comparative Example 1 |  | 0 | 0 |

(3) Hydrosilylation of Styrene with 1,1,3,3-Tetramethyldisiloxane Using Iron Compound and Isocyanide Ligand

[Example 21] Hydrosilylation Reaction Using Iron Acetate and 1-Isocyanoadamantane

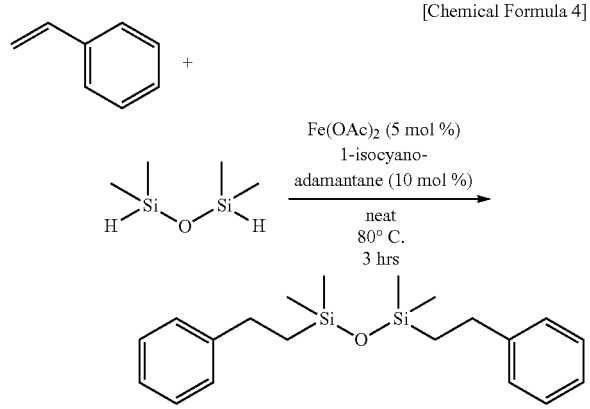

[Chemical Formula 4]

Reaction was carried out according to the same procedure as in Example 1 aside from using 115 µL (0.65 mmol) of 1,1,3,3-tetramethyldisiloxane instead of 1,1,3,3,3-pentamethyldisiloxane. As a result, it was confirmed that the signal assigned to the reactant disappeared completely. Instead, a multiplet at 0.89 ppm indicative of the signal assigned to proton on silicon-adjoining carbon in the desired product was observed, from which a yield was computed. The results are shown in Table 5.

TABLE 5

|  | Conversion (%) | Yield (%) |
|---|---|---|
| Example 21 | >99 | >99 |

(4) Hydrosilylation of Alkene with 1,1,3,3,3-Pentamethyldisiloxane Using Cobalt Acetate and Isocyanide Ligand

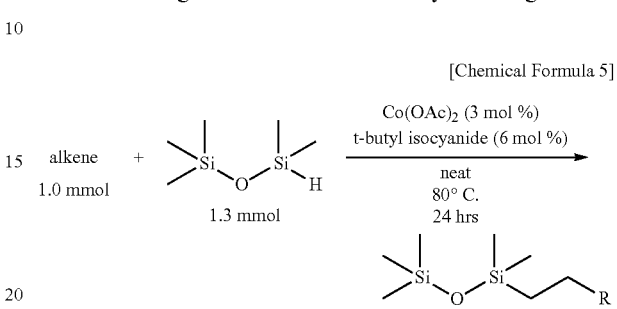

[Chemical Formula 5]

[Example 22] Hydrosilylation Reaction of 1-Octene

A screw-top vial was charged with 5 mg (0.03 mmol) of cobalt acetate (commercial product) as a catalyst, 5 mg (0.06 mmol) of t-butyl isocyanide as a ligand, 254 µL (1.3 mmol) of 1,1,3,3,3-pentamethyldisiloxane, and 157 µL (1.0 mmol) of 1-octene. The vial was closed, after which the contents were stirred at 80° C. for 24 hours. After cooling, analysis was made by $^1$H-NMR spectroscopy to determine the structure and yield of the product. As a result, it was confirmed that the signal assigned to the ethylene site of 1-octene as the reactant disappeared completely. Instead, a triplet at 0.51 ppm indicative of the signal assigned to proton on silicon-adjoining carbon in the desired product, 1,1,1,3,3-pentamethyl-3-octyldisiloxane was observed, from which a yield was computed. The results are shown in Table 6.

$^1$H-NMR (396 MHz, CDCl$_3$) δ: 0.03 (a, 6H), 0.06 (s, 9H), 0.50 (t, J=7.7 Hz, 2H), 0.88 (t, J=6.8 Hz, 3H), 1.19-1.34 (br, 12H)

[Example 23] Hydrosilylation Reaction of 2-Octene

Reaction was carried out according to the same procedure as in Example 22 aside from using 157 µL (1.0 mmol) of 2-octene instead of 1-octene. As a result, it was confirmed that the signal assigned to the ethylene site of 2-octene as the reactant diminished. Instead, a triplet at 0.51 ppm indicative of the signal assigned to proton on silicon-adjoining carbon in the desired product, 1,1,1,3,3-pentamethyl-3-octyldisiloxane was observed, from which a yield was computed. The results are shown in Table 6.

[Example 24] Hydrosilylation Reaction of Styrene

Reaction was carried out according to the same procedure as in Example 22 aside from using 115 µL (1.0 mmol) of styrene instead of 1-octene. As a result, it was confirmed that the signal assigned to the ethylene site of styrene as the reactant diminished. Instead, a multiplet at 0.89 ppm indicative of the signal assigned to proton on silicon-adjoining carbon in the desired product, 1,1,1,3,3-pentamethyl-3-phenethyldisiloxane was observed, from which a yield was computed. The results are shown in Table 6.

[Example 25] Hydrosilylation Reaction of α-Methylstyrene

Reaction was carried out according to the same procedure as in Example 22 aside from using 130 μL (1.0 mmol) of α-methylstyrene instead of 1-octene. As a result, it was confirmed that the signal assigned to the ethylene site of α-methylstyrene as the reactant diminished. Instead, a multiplet at 0.95 ppm indicative of the signal assigned to proton on silicon-adjoining carbon in the desired product, 1,1,1,3,3-pentamethyl-3-(2-phenylpropyl)disiloxane was observed, from which a yield was computed. The results are shown in Table 6.

$^1$H-NMR (396 MHz, CDCl$_3$) δ: −0.07 (s, 3H), −0.06 (s, 3H), 0.05 (s, 9H), 0.89-1.00 (m, 2H), 1.28 (d, J=7.3 Hz, 3H), 2.91 (tq, J=6.8 Hz, J=7.3 Hz, 1H), 7.13-7.32 (m, 5H)

[Example 26] Hydrosilylation Reaction of 1,1,1,3,5,5,5-Heptamethyl-3-Vinyltrisiloxane Reaction was carried out according to the same procedure as in Example 22 aside from using 249 mg (1.0 mmol) of 1,1,1,3,5,5,5-heptamethyl-3-vinyltrisiloxane instead of 1-octene. As a result, it was confirmed that the signal assigned to the ethylene site of 1,1,1,3,5,5,5-heptamethyl-3-vinyltrisiloxane as the reactant disappeared completely. Instead, a multiplet at 0.38 ppm indicative of the signal assigned to proton on silicon-adjoining carbon in the desired product, 1,1,1,3,5,5,5-heptamethyl-3-(2-(1,1,3,3,3-pentamethyldisiloxanyl)ethyl)trisiloxane was observed, from which a yield was computed. The results are shown in Table 6.

$^1$H-NMR (396 MHz, CDCl$_3$) δ: 0.00 (s, 3H), 0.03 (s, 6H), 0.06 (s, 9H), 0.09 (s, 18H), 0.38 (m, 4H)

TABLE 6

|  | Alkene | Conversion (%) | Yield (%) |
|---|---|---|---|
| Example 22 | 1-octene | >99 | 74 |
| Example 23 | 2-octene | >99 | 79 |
| Example 24 | styrene | >99 | 19 |
| Example 25 | α-methylstyrene | >99 | >99 |
| Example 26 | 1,1,1,3,5,5,5-heptamethyl-3-vinyltrisiloxane | >99 | >99 |

(5) Hydrosilylation of 1-Octene with Various Hydrosilanes Using Cobalt Acetate and Isocyanide Ligand

[Chemical Formula 6]

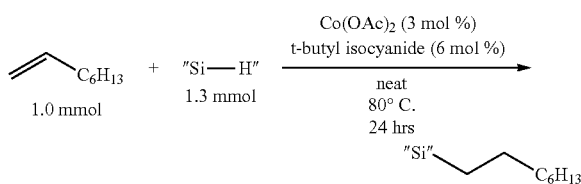

[Example 27] Hydrosilylation Reaction with Dimethylphenylsilane

Reaction was carried out according to the same procedure as in Example 22 aside from using 202 μL (1.3 mmol) of dimethylphenylsilane instead of 1,1,3,3,3-pentamethyldisiloxane. As a result, it was confirmed that the signal assigned to the reactant disappeared completely. Instead, a triplet at 0.73 ppm indicative of the signal assigned to proton on silicon-adjoining carbon in the desired product, dimethyloctylphenylsilane was observed, from which a yield was computed. The results are shown in Table 7.

$^1$H-NMR (396 MHz, CDCl$_3$) δ: 0.25 (s, 6H), 0.06 (s, 9H), 0.73 (t, J=7.7 Hz, 2H), 0.87 (t, J=6.8 Hz, 3H), 1.16-1.35 (br, 12H), 7.32-7.36 (m, 2H), 7.47-7.57 (m, 3H)

[Example 28] Hydrosilylation Reaction with 1,1,1,3,5,5,5-Heptamethyltrisiloxane Reaction was carried out according to the same procedure as in Example 22 aside from using 353 μL (1.3 mmol) of 1,1,1,3,5,5,5-heptamethyltrisiloxane instead of 1,1,3,3,3-pentamethyldisiloxane. As a result, it was confirmed that the signal assigned to the reactant disappeared completely. Instead, a triplet at 0.44 ppm indicative of the signal assigned to proton on silicon-adjoining carbon in the desired product, 1,1,1,3,5,5,5-heptamethyl-3-octyltrisiloxane was observed, from which a yield was computed. The results are shown in Table 7.

$^1$H-NMR (396 MHz, CDCl$_3$) δ: 1.35-1.23 (m, 12H), 0.90 (t, J=6.9 Hz, 3H), 0.48-0.44 (m, 2H), 0.10 (s, 18H), 0.01 (s, 3H)

[Example 29] Hydrosilylation Reaction with Phenylsilane

Reaction was carried out according to the same procedure as in Example 22 aside from using 214 mg (1.3 mmol) of phenylsilane instead of 1,1,3,3,3-pentamethyldisiloxane. As a result, it was confirmed that the signal assigned to the reactant diminished. Instead, there were observed a triplet at 4.28 ppm indicative of the signal assigned to proton on silicon in the desired product, phenyloctylsilane and a doublet at 7.57 ppm indicative of the signal assigned to proton at the meta-position relative to phenyl group. A yield thereof was computed. The results are shown in Table 7.

$^1$H-NMR (396 MHz, C$_6$D$_6$) δ: 7.58-7.54 (m, 2H), 7.24-7.19 (m, 3H), 4.52 (t, J=5.5 Hz, 2H), 1.45-1.37 (m, 2H), 0.98 (t, J=7.2 Hz, 3H), 0.83-0.80 (m, 2H)

TABLE 7

|  | Hydrosilane ("Si—H") | Conversion (%) | Yield (%) |
|---|---|---|---|
| Example 27 | dimethylphenylsilane | >99 | 82 |
| Example 28 | 1,1,1,3,5,5,5-heptamethyltrisiloxane | >99 | 50 |
| Example 29 | phenylsilane | 16 | 12 |

(6) Hydrosilylation of α-Methylstyrene with 1,1,1,3,5,5,5-Heptamethyltrisiloxane Using Cobalt Acetate and Isocyanide Ligand Example 30

[Chemical Formula 7]

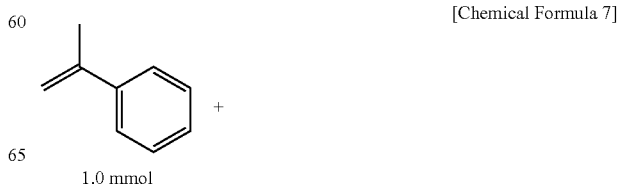

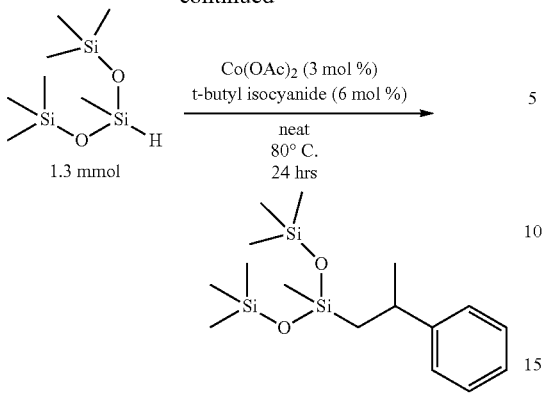

Reaction was carried out according to the same procedure as in Example 25 aside from using 353 μL (1.3 mmol) of 1,1,1,3,5,5,5-heptamethyltrisiloxane instead of 1,1,3,3,3-pentamethyldisiloxane. As a result, it was confirmed that the signal assigned to the reactant disappeared completely. Instead, a multiplet at 0.88 ppm indicative of the signal assigned to proton on silicon-adjoining carbon in the desired product, 1,1,1,3,5,5,5-heptamethyl-3-(2-phenylpropyl)trisiloxane was observed, from which a yield was computed. The results are shown in Table 8.

$^1$H-NMR (396 MHz, CDCl$_3$) δ: 7.32-7.12 (m, 5H), 2.91 (tq, J=6.8 Hz, J=7.3 Hz, 1H), 1.27 (d, J=7.3 Hz, 3H), 0.94-0.81 (m, 2H), 0.08 (s, 9H), 0.07 (s, 9H), −0.12 (s, 3H)

TABLE 8

| | Conversion (%) | Yield (%) |
|---|---|---|
| Example 30 | >99 | >99 |

(7) Hydrosilylation of 1-Octene with 1,1,3,3,3-Pentamethyldisiloxane Using Cobalt Acetate and 1-Isocyanoadamantane Example 31

[Chemical Formula 8]

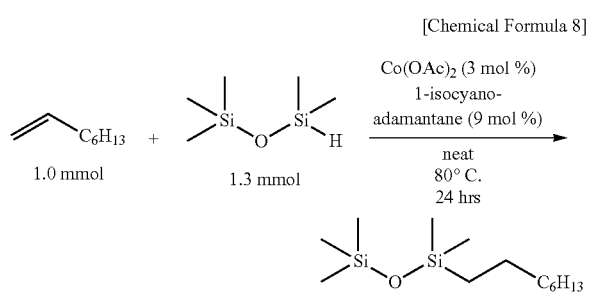

Reaction was carried out according to the same procedure as in Example 22 aside from using 15 mg (0.09 mmol) of 1-isocyanoadamantane instead of t-butyl isocyanide. As a result, it was confirmed that the signal assigned to the reactant disappeared completely. Instead, a triplet at 0.51 ppm indicative of the signal assigned to the desired product was observed, from which a yield was computed. The results are shown in Table 9.

TABLE 9

| | Conversion (%) | Yield (%) |
|---|---|---|
| Example 31 | >99 | >99 |

(8) Hydrosilylation of 1,1,1,3,5,5,5-Heptamethyl-3-Vinyltrisiloxane with 1,1,1,3,5,5,5-Heptamethyltrisiloxane Using Cobalt Acetate and 1-Isocyanoadamantane Example 32

[Chemical Formula 9]

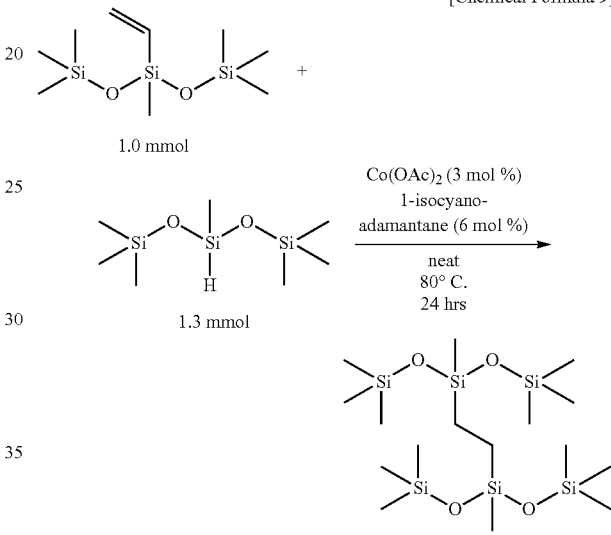

A screw-top vial was charged with 5 mg (0.03 mmol) of cobalt acetate, 10 mg (0.06 mmol) of 1-isocyanoadamantane, 353 μL (1.3 mmol) of 1,1,1,3,5,5,5-heptamethyltrisiloxane, and 249 mg (1.0 mmol) of 1,1,1,3,5,5,5-heptamethyl-3-vinyltrisiloxane. The vial was closed, after which the contents were stirred at 80° C. for 24 hours. After cooling, analysis was made by $^1$H-NMR spectroscopy to determine the structure and yield of the product. As a result, it was confirmed that the signal assigned to the ethylene site of 1,1,1,3,5,5,5-heptamethyl-3-vinyltrisiloxane as the reactant disappeared completely. Instead, a singlet at 0.35 ppm indicative of the signal assigned to proton on silicon-adjoining carbon in the desired product, 1,2-bis(1,1,1,3,5,5,5-heptamethyltrisiloxan-3-yl)ethane was observed, from which a yield was computed. The results are shown in Table 10.

$^1$H-NMR (396 MHz, CDCl$_3$) δ: 0.00 (s, 12H), 0.09 (s, 36H), 0.35 (s, 4H)

TABLE 10

| | Conversion (%) | Yield (%) |
|---|---|---|
| Example 32 | >99 | >99 |

(9) Hydrosilylation of 1-Octene with Various Hydrosilanes Using Cobalt Pivalate and 1-Isocyanoadamantane

[Chemical Formula 10]

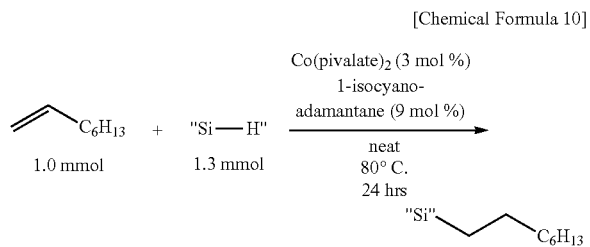

[Example 33] Hydrosilylation Reaction with 1,1,3,3,3-Pentamethyldisiloxane

Reaction was carried out according to the same procedure as in Example 31 aside from using 8 mg (0.03 mmol) of cobalt pivalate in Synthesis Example 4 instead of cobalt acetate. As a result, it was confirmed that the signal assigned to the ethylene site of 1-octene as the reactant disappeared completely. Instead, a triplet at 0.51 ppm indicative of the signal assigned to the desired product was observed, from which a yield was computed. The results are shown in Table 11.

This was followed by passage through an alumina column to remove the catalyst, and distillation under a reduced pressure (3 Pa) at 40° C., obtaining the desired product (188 mg, yield 67%).

$^{13}$C-NMR (99 MHz, CDCl$_3$) δ: 0.4, 2.0, 14.1, 18.4, 22.7, 23.3, 29.3, 29.4, 32.0, 33.4

[Example 34] Hydrosilylation Reaction with Triethylsilane

Reaction was carried out according to the same procedure as in Example 33 aside from using 151 mg (1.3 mmol) of triethylsilane instead of 1,1,3,3,3-pentamethyldisiloxane. As a result, it was confirmed that the signal assigned to the ethylene site of 1-octene as the reactant disappeared completely. Instead, a quartet at 0.50 ppm indicative of the signal assigned to proton on silicon-adjoining carbon in the desired product, triethyloctylsilane was observed, from which a yield was computed. The results are shown in Table 11.

$^1$H-NMR (396 MHz, CDCl$_3$) δ: 0.50 (q, J=7.7 Hz, 8H), 0.89 (t, J=7.7 Hz, 3H), 0.93 (t, J=7.7 Hz, 9H), 1.17-1.40 (m, 12H)

[Example 35] Hydrosilylation Reaction with Triethoxysilane

Reaction was carried out according to the same procedure as in Example 33 aside from using 214 mg (1.3 mmol) of triethoxysilane instead of 1,1,3,3,3-pentamethyldisiloxane. As a result, it was confirmed that the signal assigned to the ethylene site of 1-octene as the reactant disappeared completely. Instead, a multiplet at 0.64 ppm indicative of the signal assigned to proton on silicon-adjoining carbon in the desired product, triethoxyoctylsilane was observed, from which a yield was computed. The results are shown in Table 11.

$^1$H-NMR (396 MHz, CDCl$_3$) δ: 0.64 (m, 2H), 0.84-0.93 (m, 9H), 1.18-1.35 (m, 12H)

TABLE 11

| | Hydrosilane ("Si—H") | Conversion (%) | Yield (%) |
|---|---|---|---|
| Example 33 | 1,1,3,3,3-pentamethyldisiloxane | >99 | 99 |
| Example 34 | triethylsilane | >99 | 85 |
| Example 35 | triethoxysilane | >99 | 44 |

(10) Hydrosilylation of Alkene with 1,1,3,3,3-Pentamethyldisiloxane Using Cobalt Pivalate and 1-Isocyanoadamantane

[Chemical Formula 11]

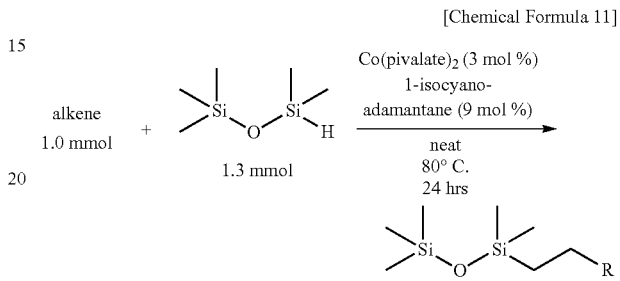

[Example 36] Hydrosilylation Reaction with Vinyltrimethylsilane

A screw-top vial was charged with 8 mg (0.03 mmol) of cobalt pivalate in Synthesis Example 4 as a catalyst, 15 mg (0.09 mmol) of 1-isocyanoadamantane as a ligand, 254 μL (1.3 mmol) of 1,1,3,3,3-pentamethyldisiloxane, and 145 μL (1.0 mmol) of vinyltrimethylsilane. The contents were stirred at 80° C. for 24 hours. After cooling, analysis was made by $^1$H-NMR spectroscopy to determine the structure and yield of the product. As a result, it was confirmed that the signal assigned to the ethylene site of vinyltrimethylsilane as the reactant disappeared completely. Instead, the signal assigned to the desired product, 1,1,1,3,3-pentamethyl-3-(2-trimethylsilylethyl)disiloxane was observed, from which a yield was computed. The results are shown in Table 12.

$^1$H-NMR (396 MHz, CDCl$_3$) δ: −0.03 (s, 9H), 0.03 (s, 6H), 0.06 (s, 9H), 0.38 (s, 4H)

[Example 37] Hydrosilylation Reaction of 2-Norbornene

Reaction was carried out according to the same procedure as in Example 36 aside from using 94 mg (1.0 mmol) of 2-norbornene instead of vinyltrimethylsilane. As a result, it was confirmed that the signal assigned to the double bond site of 2-norbornene as the reactant disappeared completely. Instead, the signal assigned to the desired product, 1-(1,1,3,3,3-pentamethyldisiloxanyl)norbornane was observed, from which a yield was computed. The results are shown in Table 12.

$^1$H-NMR (396 MHz, CDCl$_3$) δ: 2.23-2.19 (m, 2H), 1.55-1.50 (m, 2H), 1.37-1.32 (m, 1H), 1.25-1.17 (m, 4H), 1.11-1.07 (m, 1H), 0.52-0.46 (m, 1H), 0.06 (s, 9H), 0.00 (s, 3H), −0.01 (s, 3H)

[Example 38] Hydrosilylation Reaction of Allylbenzene

Reaction was carried out according to the same procedure as in Example 36 aside from using 133 μL (1.0 mmol) of allylbenzene instead of vinyltrimethylsilane. As a result, it was confirmed that the signal assigned to the ethylene site of allylbenzene as the reactant disappeared completely. Instead, the signal assigned to the desired product, 1,1,1,3,3-pentamethyl-3-(3-phenylpropyl)disiloxane was observed, from which a yield was computed. The results are shown in Table 12. There were also detected isomerized compounds, β-methylstyrene in a yield of 17% and propylbenzene in a yield of 7%.

$^1$H-NMR (396 MHz, CDCl$_3$) δ: 7.27-7.21 (m, 2H), 7.21-7.13 (m, 3H), 2.62 (t, J=6.8 Hz, 2H), 1.69-1.58 (m, 2H), 0.59-0.53 (m, 2H), 0.05 (s, 9H), 0.04 (s, 6H)

[Example 39] Hydrosilylation Reaction of 1,7-Octadiene

Reaction was carried out according to the same procedure as in Example 36 aside from using 151 μL (1.0 mmol) of 1,7-octadiene instead of vinyltrimethylsilane. As a result, it was confirmed that the signal assigned to the ethylene site of 1,7-octadiene as the reactant disappeared completely. Instead, the signal assigned to the desired product, 1,8-bis(1,1,3,3,3-pentamethyldisiloxanyl)octane was observed, from which a yield was computed. The results are shown in Table 12.

$^1$H-NMR (396 MHz, CDCl$_3$) δ: 1.34-1.19 (m, 8H), 0.89 (d, J=7.2 Hz, 4H), 0.50 (m, 4H), 0.06 (s, 18H), 0.03 (s, 12H)

TABLE 12

| | Alkene | Conversion (%) | Yield (%) |
|---|---|---|---|
| Example 36 | vinyltrimethylsilane | >99 | 85 |
| Example 37 | 2-norbornene | >99 | 90 |
| Example 38 | allylbenzene | >99 | 70 |
| Example 39 | 1,7-octadiene | >99 | >99 |

(11) Hydrosilylation of Styrene with 1,1,3,3,3-Pentamethyldisiloxane Using Cobalt Halide and Isocyanide Ligand

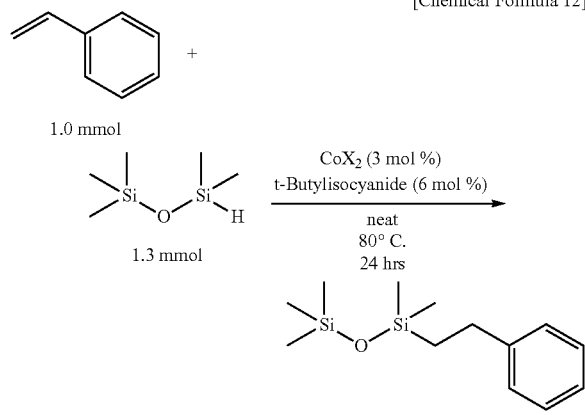

[Chemical Formula 12]

[Example 40] Hydrosilylation Reaction Using Cobalt Chloride

Reaction was carried out according to the same procedure as in Example 24 aside from using 4 mg (0.03 mmol) of cobalt chloride (commercial product) instead of cobalt acetate. As a result, it was confirmed that the signal assigned to styrene as the reactant diminished. Instead, a multiplet near 0.89 ppm indicative of the signal assigned to the desired product was observed, from which a yield was computed. The results are shown in Table 13.

[Example 41] Hydrosilylation Reaction Using Cobalt Bromide

Reaction was carried out according to the same procedure as in Example 24 aside from using 7 mg (0.03 mmol) of cobalt bromide (commercial product) instead of cobalt acetate. As a result, it was confirmed that the signal assigned to styrene as the reactant diminished. Instead, a multiplet near 0.89 ppm indicative of the signal assigned to the desired product was observed, from which a yield was computed. The results are shown in Table 13.

TABLE 13

| | Cobalt catalyst (CoX$_2$) | Conversion (%) | Yield (%) |
|---|---|---|---|
| Example 40 | cobalt chloride | 84 | 39 |
| Example 41 | cobalt bromide | 94 | 20 |

(12) Hydrosilylation of Alkene Using Compound Having Nickel-Oxygen Bond and Isocyanide Ligand

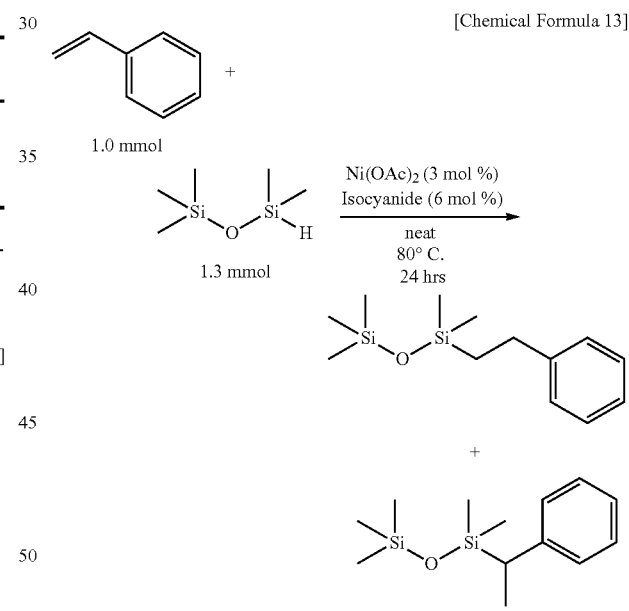

[Chemical Formula 13]

[Example 42] Hydrosilylation Reaction of Styrene with 1,1,3,3,3-Pentamethyldisiloxane Using Nickel Acetate and t-Butyl Isocyanide A screw-top vial was charged with 5 mg (0.03 mmol) of nickel acetate (commercial product), 5 mg (0.06 mmol) of t-butyl isocyanide, 254 μL (1.3 mmol) of 1,1,3,3,3-pentamethyldisiloxane, and 115 μL (1.0 mmol) of styrene. The vial was closed, after which the contents were stirred at 80° C. for 24 hours. After cooling, analysis was made by $^1$H-NMR spectroscopy to determine the structure and yield of the product. As a result, it was confirmed that the signal assigned to the reactant diminished. Instead, there were observed a multiplet near 0.89 ppm indicative of the signal assigned to proton on silicon-adjoining carbon in 1,1,1,3,3-pentamethyl-3-phenethyldisiloxane, a doublet at 1.36 ppm indicative of the signal assigned to proton on β-position carbon in 1,1,1,3,3-pentamethyl-3-(1-phenylethyl)-disiloxane having silicon added at α-position, and a quartet at 2.16 ppm indicative of the signal assigned to proton on silicon-adjoining carbon, from which yields were computed. The results are shown in Table 14.

α-adduct, ¹H-NMR (396 MHz, CDCl₃) δ: −0.01 (s, 3H), 0.00 (s, 3H), 0.02 (s, 9H), 1.36 (d, J=7.6 Hz, 2H), 2.16 (q, J=7.6 Hz, 2H), 7.06-7.11 (m, 3H), 7.17 (t, J=7.6 Hz, 2H)

[Example 43] Hydrosilylation Reaction of Styrene with 1,1,3,3,3-Pentamethyldisiloxane Using Nickel Acetate and 1-Isocyanoadamantane Reaction was carried out according to the same procedure as in Example 42 aside from using 10 mg (0.06 mmol) of 1-isocyanoadamantane instead of t-butyl isocyanide. As a result, it was confirmed that the signal assigned to styrene as the reactant disappeared completely. Instead, there were observed a multiplet at 0.89 ppm indicative of the signal assigned to 1,1,1,3,3-pentamethyl-3-phenethyldisiloxane, a doublet at 1.36 ppm and a quartet at 216 ppm indicative of the signals assigned to 1,1,1,3,3-pentamethyl-3-(1-phenylethyl)disiloxane having silicon added at α-position, from which yields were computed. The results are shown in Table 14.

TABLE 14

| Isocyanide | Conversion (%) | Yield (%) | α-adduct yield (%) |
| --- | --- | --- | --- |
| Example 42 | t-butyl isocyanide | 70 | 6 | 31 |
| Example 43 | 1-isocyanoadamantane | >99 | 73 | 27 |

(13) Hydrosilylation of Alkene Using Compound Having Ruthenium-Oxygen Bond and Isocyanide Ligand

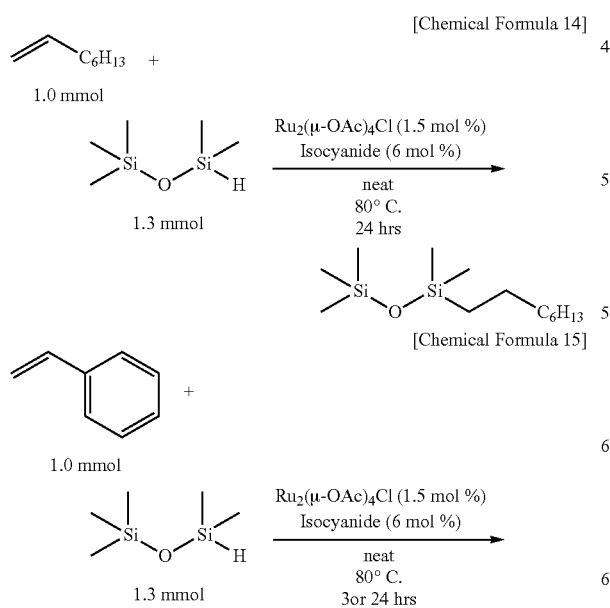

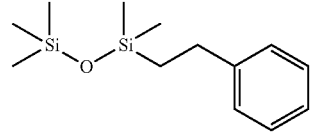

[Example 44] Hydrosilylation Reaction of 1-Octene with 1,1,3,3,3-Pentamethyldisiloxane Using Ru₂(μ-OAc)₄Cl and t-Butyl Isocyanide A screw-top vial was charged with 17 mg (0.015 mmol) of Ru₂(μ-OAc)₄Cl in Synthesis Example 6, 5 mg (0.06 mmol) of t-butyl isocyanide, 254 μL (1.3 mmol) of 1,1,3,3,3-pentamethyldisiloxane, and 157 μL (1.0 mmol) of 1-octene. The vial was closed, after which the contents were stirred at 80° C. for 24 hours. After cooling, analysis was made by ¹H-NMR spectroscopy to determine the structure and yield of the product. As a result, it was confirmed that the signal assigned to the ethylene site of 1-octene disappeared completely. Instead, a triplet at 0.51 ppm indicative of the signal assigned to proton on silicon-adjoining carbon in the desired product, 1,1,1,3,3-pentamethyl-3-octyldisiloxane was observed, from which a yield was computed. The results are shown in Table 15.

[Example 45] Hydrosilylation Reaction of 1-Octene with 1,1,3,3,3-Pentamethyldisiloxane Using Ru₂(μ-OAc)₄Cl and 1-Isocyanoadamantane Reaction was carried out according to the same procedure as in Example 44 aside from using 10 mg (0.06 mmol) of 1-isocyanoadamantane instead of t-butyl isocyanide. As a result, it was confirmed that the signal assigned to 1-octene as the reactant disappeared completely. Instead, a triplet at 0.51 ppm indicative of the signal assigned to proton on silicon-adjoining carbon of the desired product, 1,1,1,3,3-pentamethyl-3-octyldisiloxane was observed, from which a yield was computed. The results are shown in Table 15.

TABLE 15

| Isocyanide | Conversion (%) | Yield (%) |
| --- | --- | --- |
| Example 44 | t-butyl isocyanide | >99 | 4 |
| Example 45 | 1-isocyanoadamantane | >99 | 59 |

[Example 46] Hydrosilylation Reaction of Styrene with 1,1,3,3,3-Pentamethyldisiloxane Using Ru₂(μ-OAc)₄Cl and t-Butyl Isocyanide Reaction was carried out according to the same procedure as in Example 44 aside from using 115 μL (1.0 mmol) of styrene instead of 1-octene. As a result, it was confirmed that the signal assigned to styrene as the reactant disappeared completely. Instead, a multiplet near 0.90 ppm indicative of the signal assigned to proton on silicon-adjoining carbon of the desired product, 1,1,1,3,3-pentamethyl-3-octyldisiloxane was observed, from which a yield was computed. The results are shown in Table 16.

[Example 47] Hydrosilylation Reaction of Styrene with 1,1,3,3,3-Pentamethyldisiloxane Using Ru₂(μ-OAc)₄Cl and 1-Isocyanoadamantane Reaction was carried out according to the same procedure as in Example 45 aside from using 115 μL (1.0 mmol) of styrene instead of 1-octene. As a result, it was confirmed that the signal assigned to styrene as the reactant disappeared completely. Instead, a multiplet near 0.90 ppm indicative of the signal assigned to proton on silicon-adjoining carbon of the desired product, 1,1,1,3,3-pentamethyl-3-octyldisiloxane was observed, from which a yield was computed. The results are shown in Table 16.

TABLE 16

| | Isocyanide | Time (h) | Conversion (%) | Yield (%) |
|---|---|---|---|---|
| Example 46 | t-butyl isocyanide | 24 | >99 | 41 |
| Example 47 | 1-isocyanoadamantane | 3 | 81 | 16 |

(14) Hydrosilylation of Alkene Using Rhodium Compound Having Rhodium-Oxygen Bond and Isocyanide Ligand

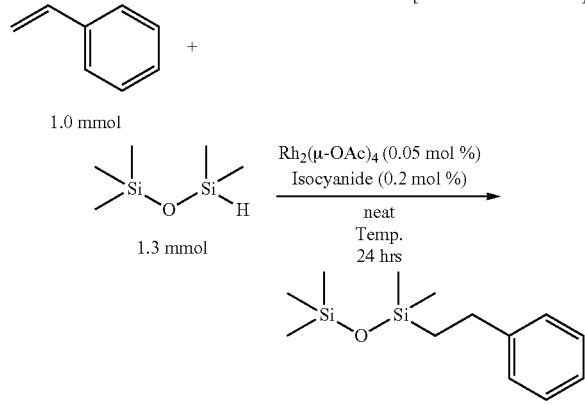

[Chemical Formula 16]

[Example 48] Hydrosilylation Reaction of Styrene with 1,1,3,3,3-Pentamethyldisiloxane Using Rhodium Acetate Dimer and t-Butyl Isocyanide A screw-top vial was charged with 2 mg (0.005 mmol) of rhodium acetate dimer (commercial product), 2 mg (0.02 mmol) of t-butyl isocyanide, 1.94 g (13.0 mmol) of 1,1,3,3,3-pentamethyldisiloxane, and 1.04 g (10.0 mmol) of styrene. The vial was closed, after which the contents were stirred at 80° C. for 24 hours. After cooling, analysis was made by $^1$H-NMR spectroscopy to determine the structure and yield of the product. As a result, it was confirmed that the signal assigned to styrene as the reactant disappeared completely. Instead, a multiplet at 0.89 ppm indicative of the signal assigned to the desired product was observed, from which a yield was computed. The results are shown in Table 17.

[Example 49] Change of Reaction Temperature from Example 48

Reaction was carried out according to the same procedure as in Example 48 aside from lowering the reaction temperature to 50° C. As a result, it was confirmed that the signal assigned to styrene as the reactant diminished. Instead, a triplet near 0.89 ppm indicative of the signal assigned to the desired product was observed, from which a yield was computed. The results are shown in Table 17.

[Example 50] Hydrosilylation Reaction of Styrene with 1,1,3,3,3-Pentamethyldisiloxane Using Rhodium Acetate Dimer and 1-Isocyanoadamantane Ligand Reaction was carried out according to the same procedure as in Example 49 aside from using 3 mg (0.02 mmol) of 1-isocyanoadamantane instead of t-butyl isocyanide. As a result, it was confirmed that the signal assigned to styrene as the reactant disappeared completely. Instead, a triplet near 0.89 ppm indicative of the signal assigned to the desired product was observed, from which a yield was computed. The results are shown in Table 17.

TABLE 17

| | Isocyanide | Temperature (° C.) | Conversion (%) | Yield (%) |
|---|---|---|---|---|
| Example 48 | t-butyl isocyanide | 80 | >99 | >99 |
| Example 49 | t-butyl isocyanide | 50 | 91 | 89 |
| Example 50 | 1-isocyanoadamantane | 50 | >99 | 98 |

[Comparative Example 2] Hydrosilylation Reaction of Styrene with 1,1,3,3,3-Pentamethyldisiloxane Using Rhodium Acetate Dimer Alone A screw-top vial was charged with 8 mg (0.015 mmol) of rhodium acetate dimer, 254 µL (1.3 mmol) of 1,1,3,3,3-pentamethyldisiloxane, and 115 µL (1.0 mmol) of styrene. The vial was closed, after which the contents were stirred at 80° C. for 24 hours. After cooling, analysis was made by $^1$H-NMR spectroscopy to determine the structure and yield of the product. As a result, it was confirmed that the signal assigned to styrene as the reactant disappeared completely. Instead, a multiplet at 0.89 ppm indicative of the signal assigned to the product was observed, from which a yield was computed. The yield of the desired product was 51%, whereas 37% of a product having silicon added at α-position and 12% of ethylbenzene were detected as by-products.

These results demonstrate that the desired product is selectively obtained by adding an isocyanide ligand to rhodium acetate dimer.

(15) Hydrosilylation Reaction of Styrene with 1,1,3,3,3-Pentamethyldisiloxane Using Iron Pivalate and Various Isocyanide Ligands

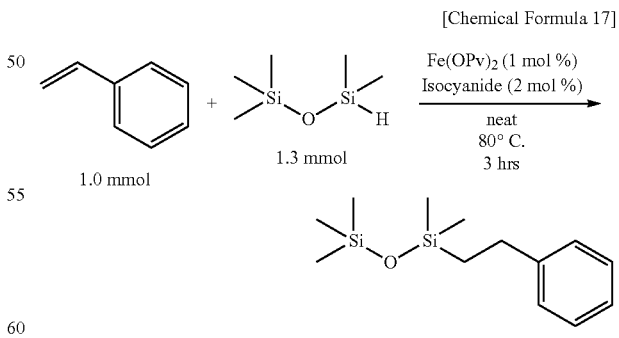

[Chemical Formula 17]

[Example 51] Hydrosilylation Reaction Using Iron Pivalate and n-Butyl Isocyanide A screw-top vial was charged with 3 mg (0.01 mmol) of iron pivalate in Synthesis Example 1 as a catalyst, 2 µL (0.02 mmol) of n-butyl isocyanide as an isocyanide ligand, 254 μL (1.3 mmol) of 1,1,3,3,3-pentamethyldisiloxane as a hydrosilane, and 115 μL (1.0 mmol) of styrene. The contents were stirred at 80° C. for 3 hours. After cooling, analysis was made by ¹H-NMR spectroscopy to determine the structure and yield of the product. As a result, it was confirmed that the signal assigned to the reactant disappeared completely. Instead, a multiplet at 0.89 ppm indicative of the signal assigned to proton on silicon-adjoining carbon in the desired product was observed, from which a yield was computed. The results are shown in Table 18.

[Example 52] Hydrosilylation Reaction Using Iron Pivalate and 1,1,3,3-Tetramethylbutyl Isocyanide A screw-top vial was charged with 3 mg (0.01 mmol) of iron pivalate in Synthesis Example 1 as a catalyst, 4 μL (0.02 mmol) of 1,1,3,3-tetramethylbutyl isocyanide as an isocyanide ligand, 254 μL (1.3 mmol) of 1,1,3,3,3-pentamethyldisiloxane as a hydrosilane, and 115 μL (1.0 mmol) of styrene. The contents were stirred at 80° C. for 3 hours. After cooling, analysis was made by ¹H-NMR spectroscopy to determine the structure and yield of the product. As a result, it was confirmed that the signal assigned to the reactant diminished. Instead, a multiplet at 0.89 ppm indicative of the signal assigned to proton on silicon-adjoining carbon in the desired product was observed, from which a yield was computed. The results are shown in Table 18.

[Example 53] Hydrosilylation Reaction Using Iron Pivalate and Cyclohexyl Isocyanide A screw-top vial was charged with 3 mg (0.01 mmol) of iron pivalate in Synthesis Example 1 as a catalyst, 2 μL (0.02 mmol) of cyclohexyl isocyanide as an isocyanide ligand, 254 μL (1.3 mmol) of 1,1,3,3,3-pentamethyldisiloxane as a hydrosilane, and 115 μL (1.0 mmol) of styrene. The contents were stirred at 80° C. for 3 hours. After cooling, analysis was made by ¹H-NMR spectroscopy to determine the structure and yield of the product. As a result, it was confirmed that the signal assigned to the reactant disappeared completely. Instead, a multiplet at 0.89 ppm indicative of the signal assigned to proton on silicon-adjoining carbon in the desired product was observed, from which a yield was computed. The results are shown in Table 18.

[Example 54] Hydrosilylation Reaction Using Iron Pivalate and 4-Tolyl Isocyanide A screw-top vial was charged with 3 mg (0.01 mmol) of iron pivalate in Synthesis Example 1 as a catalyst, 2 mg (0.02 mmol) of 4-tolyl isocyanide as an isocyanide ligand, 254 μL (1.3 mmol) of 1,1,3,3,3-pentamethyldisiloxane as a hydrosilane, and 115 μL (1.0 mmol) of styrene. The contents were stirred at 80° C. for 3 hours. After cooling, analysis was made by ¹H-NMR spectroscopy to determine the structure and yield of the product. As a result, it was confirmed that the signal assigned to the reactant diminished. Instead, a multiplet at 0.89 ppm indicative of the signal assigned to proton on silicon-adjoining carbon in the desired product was observed, from which a yield was computed. The results are shown in Table 18.

TABLE 18

| | Isocyanide | Conversion (%) | Yield (%) |
|---|---|---|---|
| Example 51 | n-butyl isocyanide | >99 | 92 |
| Example 52 | 1,1,3,3-tetramethylbutyl isocyanide | 89 | 15 |
| Example 53 | cyclohexyl isocyanide | >99 | 75 |
| Example 54 | 4-tolyl isocyanide | 14 | 14 |

(16) Hydrosilylation Reaction of α-Methylstyrene with 1,1,3,3,3-Pentamethyldisiloxane Using Cobalt Pivalate and Various Isocyanide Ligands

[Chemical Formula 18]

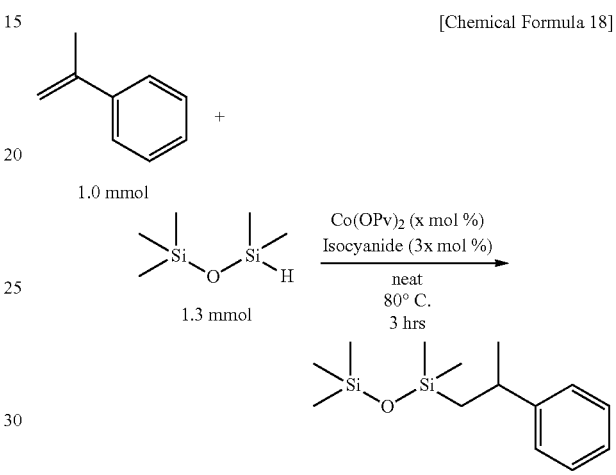

[Example 55] Hydrosilylation Reaction Using Cobalt Pivalate and n-Butyl Isocyanide A screw-top vial was charged with 3 mg (0.01 mmol) of cobalt pivalate in Synthesis Example 4 as a catalyst, 3 μL (0.03 mmol) of n-butyl isocyanide as an isocyanide ligand, 254 μL (1.3 mmol) of 1,1,3,3,3-pentamethyldisiloxane as a hydrosilane, and 130 μL (1.0 mmol) of α-methylstyrene. The contents were stirred at 80° C. for 3 hours. After cooling, analysis was made by ¹H-NMR spectroscopy to determine the structure and yield of the product. As a result, it was confirmed that the signal assigned to the reactant diminished. Instead, a multiplet near 2.92 ppm indicative of the signal assigned to proton on silicon-adjoining carbon in the desired product was observed, from which a yield was computed. The results are shown in Table 19.

[Example 56] Hydrosilylation Reaction Using Cobalt Pivalate and 1,1,3,3-Tetramethylbutyl Isocyanide A screw-top vial was charged with 3 mg (0.01 mmol) of cobalt pivalate in Synthesis Example 4 as a catalyst, 6 μL (0.03 mmol) of 1,1,3,3-tetramethylbutyl isocyanide as an isocyanide ligand, 254 μL (1.3 mmol) of 1,1,3,3,3-pentamethyldisiloxane as a hydrosilane, and 130 μL (1.0 mmol) of α-methylstyrene. The contents were stirred at 80° C. for 3 hours. After cooling, analysis was made by ¹H-NMR spectroscopy to determine the structure and yield of the product. As a result, it was confirmed that the signal assigned to the reactant diminished. Instead, a multiplet near 2.92 ppm indicative of the signal assigned to proton on silicon-adjoining carbon in the desired product was observed, from which a yield was computed. The results are shown in Table 19.

[Example 57] Hydrosilylation Reaction Using Cobalt Pivalate and Cyclohexyl Isocyanide A screw-top vial was charged with 3 mg (0.01 mmol) of cobalt pivalate in Synthesis Example 4 as a catalyst, 3 μL (0.03 mmol) of cyclohexyl isocyanide as an isocyanide ligand, 254 μL (1.3 mmol) of 1,1,3,3,3-pentamethyldisiloxane as a hydrosilane, and 130 μL (1.0 mmol) of α-methylstyrene. The contents were stirred at 80° C. for 3 hours. After cooling, analysis was made by $^1$H-NMR spectroscopy to determine the structure and yield of the product. As a result, it was confirmed that the signal assigned to the reactant disappeared completely. Instead, a multiplet near 2.92 ppm indicative of the signal assigned to proton on silicon-adjoining carbon in the desired product was observed, from which a yield was computed. The results are shown in Table 19.

[Example 58] Hydrosilylation Reaction Using Cobalt Pivalate and 4-Tolyl Isocyanide A screw-top vial was charged with 3 mg (0.01 mmol) of cobalt pivalate in Synthesis Example 4 as a catalyst, 3 mg (0.03 mmol) of 4-tolyl isocyanide as an isocyanide ligand, 254 μL (1.3 mmol) of 1,1,3,3,3-pentamethyldisiloxane as a hydrosilane, and 130 μL (1.0 mmol) of α-methylstyrene. The contents were stirred at 80° C. for 3 hours. After cooling, analysis was made by $^1$H-NMR spectroscopy to determine the structure and yield of the product. As a result, it was confirmed that the signal assigned to the reactant diminished. Instead, a multiplet near 2.92 ppm indicative of the signal assigned to proton on silicon-adjoining carbon in the desired product was observed, from which a yield was computed. The results are shown in Table 19.

[Example 59] Hydrosilylation Reaction Using Cobalt Pivalate and Mesityl Isocyanide A screw-top vial was charged with 9 mg (0.03 mmol) of cobalt pivalate in Synthesis Example 4 as a catalyst, 13 mg (0.09 mmol) of mesityl isocyanide as an isocyanide ligand, 254 μL (1.3 mmol) of 1,1,3,3,3-pentamethyldisiloxane as a hydrosilane, and 130 μL (1.0 mmol) of α-methylstyrene. The contents were stirred at 80° C. for 3 hours. After cooling, analysis was made by $^1$H-NMR spectroscopy to determine the structure and yield of the product. As a result, it was confirmed that the signal assigned to the reactant diminished. Instead, a multiplet near 2.92 ppm indicative of the signal assigned to proton on silicon-adjoining carbon in the desired product was observed, from which a yield was computed. The results are shown in Table 19.

TABLE 19

| | Catalyst amount (%) | Isocyanide | Conversion (%) | Yield (%) |
|---|---|---|---|---|
| Example 55 | 1 | n-butyl isocyanide | 81 | 81 |
| Example 56 | 1 | 1,1,3,3-tetramethylbutyl isocyanide | 44 | 44 |
| Example 57 | 1 | cyclohexyl isocyanide | >99 | >99 |
| Example 58 | 1 | 4-tolyl isocyanide | 20 | 17 |
| Example 59 | 3 | mesityl isocyanide | 88 | 81 |

[Synthesis Example 8] Synthesis of Cobalt Carboxylate A

A 1 L flask equipped with a reflux tube was charged with 184.0 g (1.0 mol) of 10-undecylenic acid and 150.0 g of toluene and heated at 80° C. Then 100.6 g (0.625 mol) of hexamethyldisilazane was added dropwise to the solution, which was heated at 80° C. for a further 3 hours. The volatile component was removed by heating at 100° C. in vacuum, obtaining $CH_3$=$CH(CH_2)_8COOSiMe_2$ (Silylated product A) (254.4 g, yield 99.4%).

A 1 L flask equipped with a reflux tube was charged with 254.4 g (0.99 mol) of Silylated product A and 100.0 g of toluene and heated at 90° C. To the solution, 0.5 g of a toluene solution of 0.5 wt % chloroplatinic acid was added, and 264.7 g (1.19 mol) of 1,1,1,3,5,5,5-heptamethyltrisiloxane was added dropwise. At the end of dropwise addition, the solution was heated at 100° C. for a further 2 hours. The volatile component was removed by heating at 120° C. in vacuum, obtaining $(Me_3SiO)_2MeSi(CH_2)_{10}COOSiMe_3$ (Adduct A) (451.2 g, yield 95.0%).

A 1 L flask was charged with 239.0 g (0.5 mol) of Adduct A and 140.0 g of methanol, which were stirred at room temperature for 14 hours. Distillation gave the desired product: $(Me_2SiO)_2MeSi(CH_3)_{10}COOH$ (boiling point 175.0-176.0° C./0.3 kPa, amount 162.4 g, yield 80.0%). It had a purity of 99.5% as measured by gas chromatography.

Figure 3:
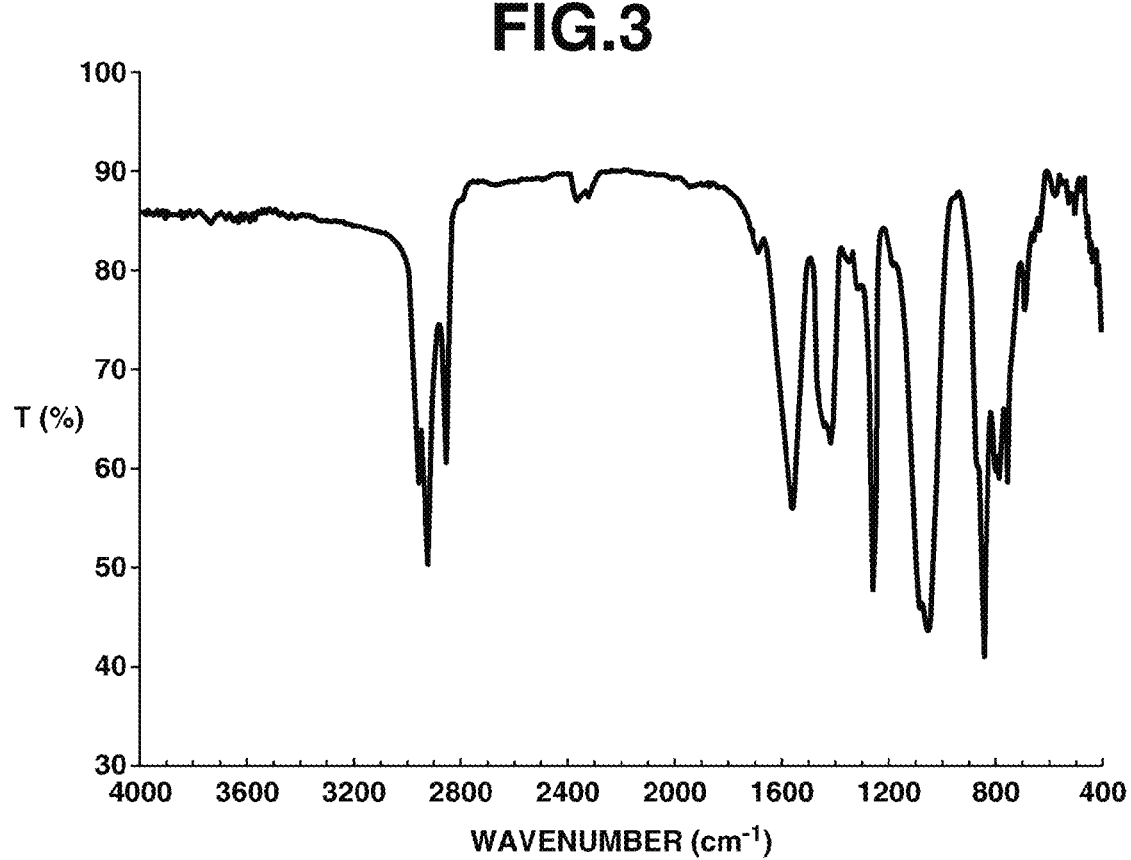
FIG. 3 is a diagram of the FT-IR spectrum of cobalt carboxylate A obtained in Synthesis Example 8.

Next, in a 20 mL recovery flask, 0.43 g (2.41 mmol) of cobalt acetate and 2.0 g (4.92 mmol) of $(Me_3SiO)_2MeSi(CH_2)_{10}COOH$ obtained above were fed and stirred at 180° C. for 1 hour. Thereafter, the reaction mixture was vacuum dried at the temperature for 1 hour, obtaining cobalt carboxylate A. The FT-IR spectrum of cobalt carboxylate A is shown in FIG. 3.

FT-IR (KBr) v:
2958, 2924, 2583, 1555, 1413, 1257, 1078, 1049, 842, 799, 783, 754, 687

(17) Hydrosilylation Reaction of α-Methylstyrene Using Cobalt Carboxylate A and 1-Isocyanoadamantane

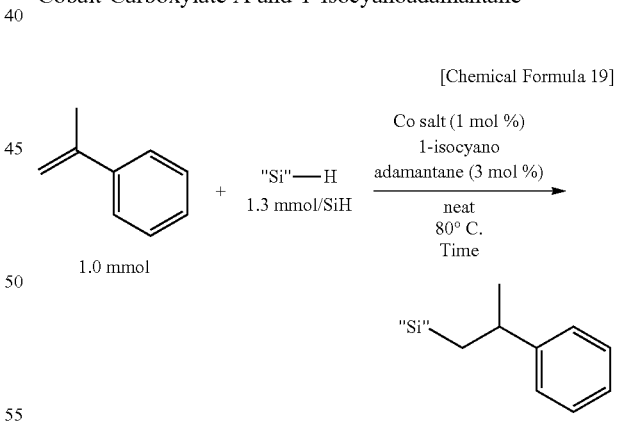

[Chemical Formula 19]

[Example 60] Hydrosilylation Reaction of α-Methylstyrene with 1,1,3,3,3-Pentamethyldisiloxane Using Cobalt Carboxylate A and 1-Isocyanoadamantane A screw-top vial was charged with 9 mg (0.01 mmol) of cobalt carboxylate A in Synthesis Example 8 as a catalyst, 5 mg (0.03 mmol) of 1-isocyanoadamantane as an isocyanide ligand, 254 μL (1.3 mmol) of 1,1,3,3,3-pentamethyldisiloxane as a hydrosilane, and 130 μL (1.0 mmol) of α-methylstyrene. The contents were stirred at 80° C. for 3 hours. After cooling, analysis was made by ¹H-NMR spectroscopy to determine the structure and yield of the product. As a result, it was confirmed that the signal assigned to the reactant disappeared. Instead, a multiplet near 2.92 ppm indicative of the signal assigned to proton on silicon-adjoining carbon in the desired product was observed, from which a yield was computed. The results are shown in Table 20.

[Example 61] Hydrosilylation Reaction of α-Methylstyrene with Dual End Hydrosilane-Terminated Polydimethylsiloxane Using Cobalt Carboxylate A and 1-Isocyanoadamantane A screw-top vial was charged with 9 mg (0.01 mmol) of cobalt carboxylate A in Synthesis Example 8 as a catalyst, 5 mg (0.03 mmol) of 1-isocyanoadamantane as an isocyanide ligand, 1.39 g (0.65 mmol) of dual end hydrosilane-terminated polydimethylsiloxane (degree of polymerization 27) as a hydrosilane, and 130 μL (1.0 mmol) of α-methylstyrene. The contents were stirred at 80° C. for 24 hours. After cooling, analysis was made by ¹H-NMR spectroscopy to determine the structure and yield of the product. As a result, it was confirmed that the signal assigned to the reactant disappeared. Instead, a multiplet near 2.92 ppm indicative of the signal assigned to proton on silicon-adjoining carbon in the desired product was observed, from which a yield was computed. The results are shown in Table 20.

TABLE 20

| | Cobalt salt | Hydrosilane | Reaction time (h) | Conversion (%) | Yield (%) |
|---|---|---|---|---|---|
| Example 60 | cobalt, carboxylate A | 1,1,3,3,3-pentamethyl-disiloxane | 3 | 98 | 98 |
| Example 61 | cobalt, carboxylate A | dual end hydrosilane-terminated polydimethyl-siloxane (DOP 27) | 24 | >99 | >99 |

(18) Hydrosilylation Reaction of 1-Octene Using Cobalt Carboxylate A and 1-Isocyanoadamantane

[Chemical Formula 20]

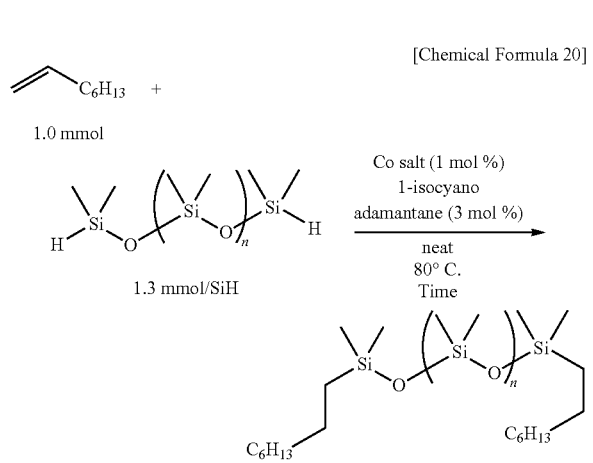

[Example 62] Hydrosilylation Reaction of 1-Octene with Dual End Hydrodimethylsiloxy-Blocked Polydimethylsiloxane Using Cobalt Carboxylate A and 1-Isocyanoadamantane A screw-top vial was charged with 9 mg (0.01 mmol) of cobalt carboxylate A in Synthesis Example 8 as a catalyst, 5 mg (0.03 mmol) of 1-isocyanoadamantane as an isocyanide ligand, 1.39 g (0.65 mmol) of dual end hydrosilane-terminated polydimethylsiloxane (DOP 27) as a hydrosilane, and 157 μL (1.0 mmol) of 1-octene. The contents were stirred at 80° C. for 25 hours. After cooling, analysis was made by ¹H-NMR spectroscopy to determine the structure and yield of the product. As a result, it was confirmed that the signal assigned to the reactant disappeared. Instead, a multiplet near 0.51 ppm indicative of the signal assigned to proton on silicon-adjoining carbon in the desired product was observed, from which a yield was computed. The results are shown in Table 21.

TABLE 21

| | Cobalt salt | Hydrosilane | Reaction time (h) | Conversion (%) | Yield (%) |
|---|---|---|---|---|---|
| Example 62 | cobalt, carboxylate A | dual end hydro-dimethylsiloxy-blocked polydimethyl-ailoxane (DOP 27) | 25 | >99 | >99 |

(19) Hydrosilylation Reaction of Alkene with Dual End Hydrodimethylsiloxy-Blocked Polydimethylsiloxane Using Metal Pivalate

[Chemical Formula 21]

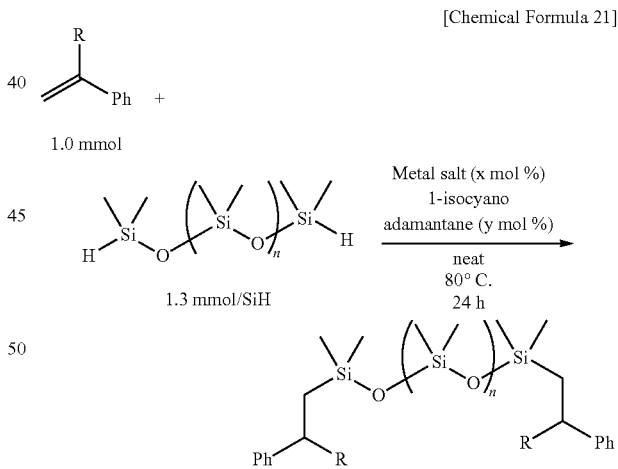

R = H or Me

Example 63

A screw-top vial was charged with 8 mg (0.03 mmol) of iron pivalate in Synthesis Example 1 as a catalyst, 10 mg (0.06 mmol) of 1-isocyanoadamantane as an isocyanide ligand, 1.39 g (0.65 mmol) of dual end hydrodimethylsiloxy-blocked polydimethylsiloxane (DOP 27) as a hydrosilane, and 115 μL (1.0 mmol) of styrene. The contents were stirred at 80° C. for 24 hours. After cooling, analysis was made by $^1$H-NMR spectroscopy to determine the structure and yield of the product. As a result, it was confirmed that the signal assigned to the reactant disappeared. Instead, a multiplet near 0.89 ppm indicative of the signal assigned to proton on silicon-adjoining carbon in the desired product was observed, from which a yield was computed. The results are shown in Table 22.

Example 64

A screw-top vial was charged with 3 mg (0.01 mmol) of cobalt pivalate in Synthesis Example 4 as a catalyst, 5 mg (0.03 mmol) of 1-isocyanoadamantane as an isocyanide ligand, 1.39 g (0.65 mmol) of dual end hydrodimethylsiloxy-blocked polydimethylsiloxane (DOP 27) as a hydrosilane, and 130 μL (1.0 mmol) of α-methylstyrene. The contents were stirred at 80° C. for 24 hours. After cooling, analysis was made by $^1$H-NMR spectroscopy to determine the structure and yield of the product. As a result, it was confirmed that the signal assigned to the reactant disappeared. Instead, a multiplet near 2.92 ppm indicative of the signal assigned to proton on silicon-adjoining carbon in the desired product was observed, from which a yield was computed. The results are shown in Table 22.

TABLE 22

| Metal salt (catalyst amount mol %) | Isocyanide amount (mol %) | Conversion (%) | Yield (%) |
| --- | --- | --- | --- |
| Example 63 | iron pivalate (3) | 6 | >99 | 65 |
| Example 64 | cobalt pivalate (1) | 3 | >99 | >99 |

[Synthesis Example 9] Synthesis of Cobalt Carboxylate B

A 500 mL flask equipped with a reflux tube was charged with 100.0 g (1.16 mol) of 3-butenoic acid and 80.0 g of hexane and heated at 70° C. Then 117.0 g (0.73 mol) of hexamethyldisilazane was added dropwise to the solution, which was heated at 70° C. for a further 3 hours. The reaction solution was distilled, obtaining the desired compound $CH_2=CHCH_2COOSiMe_3$ (Silylated product B) (b.p. 60.0-62.0° C./5.3 kPa, amount 155.1 g, yield 84.6%). It had a purity of 94.4% as measured by gas chromatography.

A 500 mL flask equipped with a reflux tube was charged with 155.1 g (0.98 mol) of Silylated product B and 150.0 g of toluene and heated at 90° C. To the solution, 0.5 g of a toluene solution of 0.5 wt % chloroplatinic acid was added, and 239.8 g (1.08 mol) of 1,1,1,3,5,5,5-heptamethyltrisiloxane was added dropwise. At the end of dropwise addition, the solution was heated at 100° C. for a further 2 hours. The reaction solution was distilled, obtaining the desired product: $(Me_3SiO)_2MeSi(CH_2)_3COOSiMe_3$ (Adduct B) (b.p. 97.0-98.5° C./0.3 kPa, amount 253.8 g, yield 68.1%). It had a purity of 98.7% as measured by gas chromatography.

Next, a 500 mL flask was charged with 207.5 g (0.55 mol) of Adduct B and 100.0 g of methanol, which were stirred at room temperature for 14 hours. Distillation gave the desired product: $(Me_3SiO)_2MeSi(CH_2)_3COOH$ (b.p. 119.5-121.0° C./0.3 kPa, amount 109.5 g, yield 64.6%). It had a purity of 98.9% as measured by gas chromatography.

Figure 4:
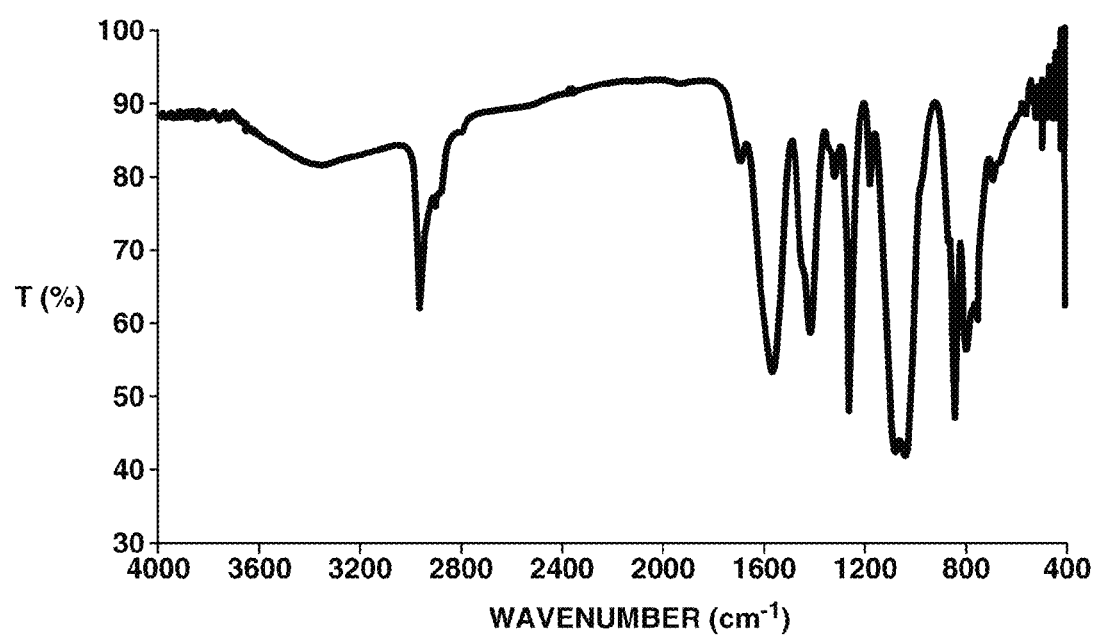
FIG. 4 is a diagram of the FT-IR spectrum of cobalt carboxylate B obtained in Synthesis Example 9.

In a 20 mL recovery flask, 0.20 g (1.13 mmol) of cobalt acetate and 0.70 g (2.28 mmol) of $(Me_3SiO)_2MeSi(CH_2)_3COOH$ obtained above were fed and stirred at 160° C. for 1 hour. Thereafter, the reaction mixture was vacuum dried at the temperature for 1 hour, obtaining cobalt carboxylate B. The FT-IR spectrum of cobalt carboxylate B is shown in FIG. 4.

FT-IR (KBr) ν:
2958, 2901, 2880, 1686, 1561, 1413, 1259, 1176, 1078, 1041, 842, 797, 755

[Synthesis Example 10] Synthesis of Cobalt Carboxylate C

A 1 L flask equipped with a reflux tube was charged with 184.0 g (1.0 mol) of 10-undecylenic acid and 150.0 g of toluene and heated at 80° C. Then 100.6 g (0.625 mol) of hexamethyldisilazane was added dropwise to the solution, which was heated at 80° C. for a further 3 hours. The volatile component was removed by heating at 100° C. in vacuum, obtaining $CH_3=CH(CH_2)_8COOSiMe_2$ (identical with Silylated product A in Synthesis Example 8) (amount 254.3 g, yield 99.3%).

A 1 L flask equipped with a reflux tube was charged with 51.2 g (0.20 mol) of Silylated product A and heated at 90° C. To the flask, 0.2 g of a toluene solution of 0.5 wt % chloroplatinic acid was added, and 94.5 g (0.23 mol) of $nBu(Me_2)SiO(Me_2SiO)_3Si(Me_2)H$ was added dropwise. At the end of dropwise addition, the solution was heated at 100° C. for a further 2 hours. The unreacted fractions were removed by heating at 200° C. in vacuum, obtaining the desired product: $nBu(Me_3)SiO(Me_2SiO)_3Si(Me_2)(CH_2)_{10}COOSiMe_3$ (Adduct C) (amount 127.0 g, yield 95.0%).

A 500 mL flask was charged with 127.0 g (0.19 mol) of Adduct C and 100.0 g of methanol, which were stirred at room temperature for 14 hours. The volatile component was removed by heating at 100° C. in vacuum, obtaining the desired product: $nBu(Me_3)SiO(Me_2SiO)_3Si(Me_2)(CH_2)_{10}COOH$ (amount 111.0 g, yield 98.0%). It had a purity of 99.8% as measured by gas chromatography.

Figure 5:
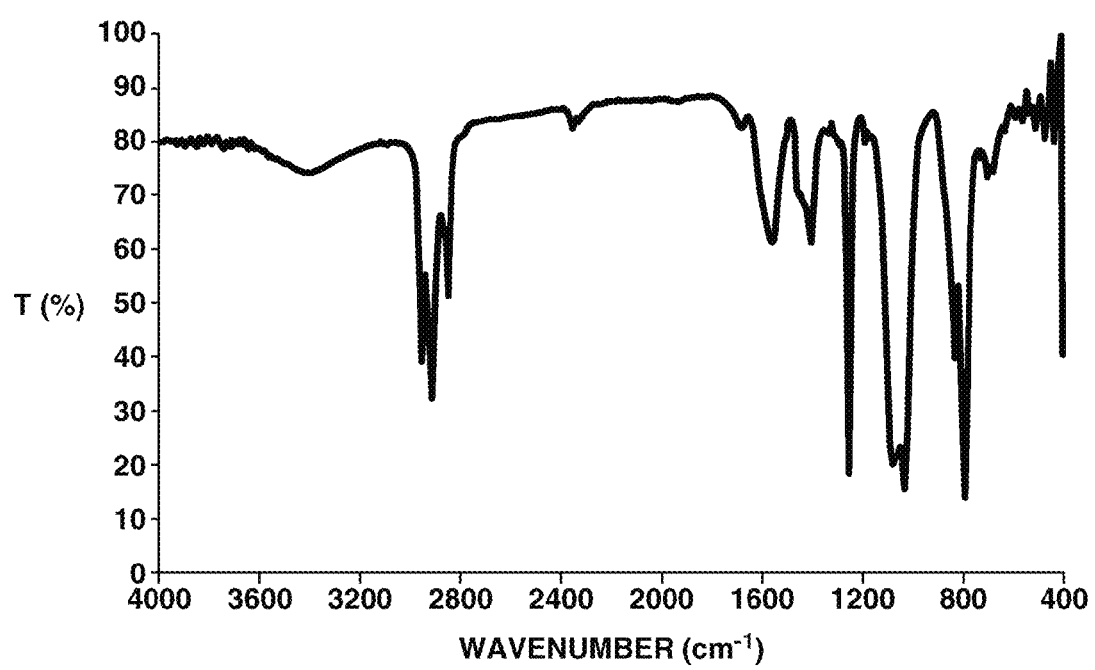
FIG. 5 is a diagram of the FT-IR spectrum of cobalt carboxylate C obtained in Synthesis Example 10.

In a 20 mL recovery flask, 0.20 g (1.13 mmol) of cobalt acetate and 1.35 g (2.26 mmol) of $nBu(Me_2)SiO(Me_2SiO)_3Si(Me_2)(CH_2)_{10}COOH$ were fed and stirred at 160° C. for 1 hour. Thereafter, the reaction mixture was vacuum dried at the temperature for 1 hour, obtaining cobalt carboxylate C. The FT-IR spectrum of cobalt carboxylate C is shown in FIG. 5.

FT-IR (KBr) ν:
2960, 2924, 2854, 1560, 1457, 1412, 1259, 1088, 1037, 840, 798

(20) Hydrosilylation Reaction of α-Methylstyrene with 1,1,3,3,3-Pentamethyldisiloxane Using Cobalt Carboxylate B or C and 1-Isocyanoadamantane

[Chemical Formula 22]

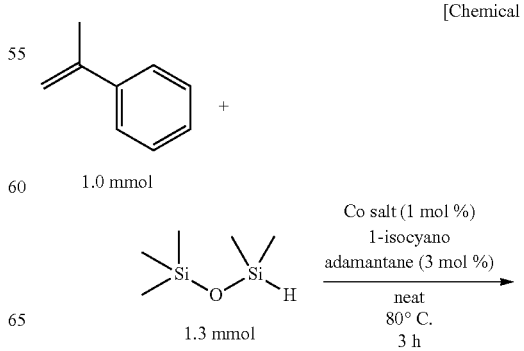

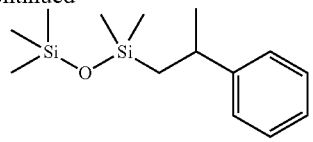

[Example 65] Hydrosilylation Reaction of α-Methylstyrene with 1,1,3,3,3-Pentamethyldisiloxane Using Cobalt Carboxylate B and 1-Isocyanoadamantane A screw-top vial was charged with 7 mg (0.01 mmol) of cobalt carboxylate B in Synthesis Example 9 as a catalyst, 5 mg (0.03 mmol) of 1-isocyanoadamantane as an isocyanide ligand, 254 μL (1.3 mmol) of 1,1,3,3,3-pentamethyldisiloxane as a hydrosilane, and 130 μL (1.0 mmol) of α-methylstyrene. The contents were stirred at 80° C. for 3 hours. After cooling, analysis was made by ¹H-NMR spectroscopy to determine the structure and yield of the product. As a result, it was confirmed that the signal assigned to the reactant disappeared. Instead, a multiplet near 2.92 ppm indicative of the signal assigned to proton on silicon-adjoining carbon in the desired product was observed, from which a yield was computed. The results are shown in Table 23.

[Example 66] Hydrosilylation Reaction of α-Methylstyrene with 1,1,3,3,3-Pentamethyldisiloxane Using Cobalt Carboxylate C and 1-Isocyanoadamantane A screw-top vial was charged with 13 mg (0.01 mmol) of cobalt carboxylate C in Synthesis Example 10 as a catalyst, 5 mg (0.03 mmol) of 1-isocyanoadamantane as an isocyanide ligand, 254 μL (1.3 mmol) of 1,1,3,3,3-pentamethyldisiloxane as a hydrosilane, and 130 μL (1.0 mmol) of α-methylstyrene. The contents were stirred at 80° C. for 3 hours. After cooling, analysis was made by ¹H-NMR spectroscopy to determine the structure and yield of the product. As a result, it was confirmed that the signal assigned to the reactant disappeared. Instead, a multiplet near 2.92 ppm indicative of the signal assigned to proton on silicon-adjoining carbon in the desired product was observed, from which a yield was computed. The results are shown in Table 23.

TABLE 23

| | Cobalt salt | Conversion (%) | Yield (%) |
|---|---|---|---|
| Example 65 | cobalt carboxylate B | 19 | 19 |
| Example 66 | cobalt carboxylate C | 92 | 92 |

(21) Hydrosilylation Reaction of α-Methylstyrene with 1,1,3,3,3-Pentamethyldisiloxane Using Cobalt Carboxylate A and Various Isocyanide Ligands

[Chemical Formula 23]

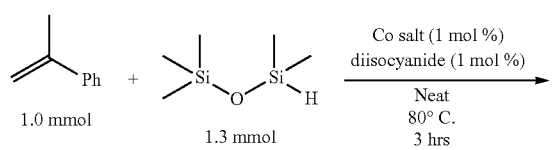

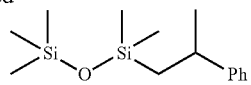

[Example 67] Hydrosilylation Reaction Using 1,6-Diisocyanohexane as Diisocyanide Ligand A reactor was charged with 9 mg (0.01 mmol) of cobalt carboxylate A in Synthesis Example 8, 1 mg (0.01 mmol) of 1,6-diisocyanohexane, 130 μL (1.0 mmol) of α-methylstyrene, and 255 μL (1.3 mmol) of 1,1,3,3,3-pentamethyldisiloxane. The contents were stirred at 80° C. for 3 hours. At the end of reaction, analysis was made by ¹H-NMR spectroscopy to determine the structure and yield of the product. As a result, it was confirmed that the signal assigned to the reactant diminished. Instead, a multiplet at 2.92 ppm indicative of the signal assigned to proton on silicon-adjoining carbon in the desired product was observed, from which a yield was computed. The results are shown in Table 24.

[Example 68] Hydrosilylation Reaction Using 1,8-Diisocyanooctane as Diisocyanide Ligand Reaction was carried out according to the same procedure as in Example 67 aside from using 2 mg (0.01 mmol) of 1,8-diisocyanooctane as the diisocyanide ligand. At the end of reaction, analysis was made by ¹H-NMR spectroscopy to determine the structure and yield of the product. As a result, it was confirmed that the signal assigned to the reactant disappeared completely. Instead, a multiplet at 2.92 ppm indicative of the signal assigned to proton on silicon-adjoining carbon in the desired product was observed, from which a yield was computed. The results are shown in Table 24.

TABLE 24

| | Cobalt salt | Diisocyanide | Conversion (%) | Yield (%) |
|---|---|---|---|---|
| Example 67 | cobalt carboxylate A | 1,6-diisocyanohexane | 8 | 8 |
| Example 68 | cobalt carboxylate A | 1,8-diisocyanooctane | 19 | 19 |

The invention claimed is:
1. A hydrosilylation reaction catalyst which is prepared from:

a metal salt compound having the formula (1):

$$M_a(L)_b(X)_c \qquad (1)$$

wherein (i) M is Fe, Co or Ni, a is 1, b is 2, and c is 0; (ii) M is Rh, a is 2, b is 4, and c is or (iii) M is Ru, a is 2, b is 4, and c is 1, X is a halogen atom, L is a monovalent organic group of at least one type selected from the formulae (3) to (5), $$-O-R^1 \qquad (3)$$

$$-OCO-R^1 \qquad (4)$$

$$-OSO_2-R^1 \qquad (5)$$

wherein $R^1$ is each independently an optionally substituted, $C_1$-$C_{30}$ monovalent organic group which may be separated by at least one atom selected from oxygen, nitrogen, sulfur and phosphorus, or a monovalent organic group having the formula (6):

$$-(A)_p\text{-}R^2 \qquad (6)$$

wherein A is an optionally substituted, $C_1$-$C_{30}$ divalent organic group which may be separated by at least one atom selected from oxygen, nitrogen, sulfur and phosphorus, p is an integer of 0 or 1, satisfying p=0 or 1 when L is a monovalent organic group having formula (3), and p=1 when L is a monovalent organic group having formula (4) or (5), $R^2$ is a group having the formula (7):

$$-\{Si(R^3)_2-R^4\}_s-Si(R^3)_d\{[(OSi(R^3)_2)]_f-R^3\}_e \qquad (7)$$

wherein $R^3$ is each independently an optionally substituted, $C_1$-$C_{20}$ alkyl group, $C_1$-$C_{20}$ alkoxy group, $C_6$-$C_{20}$ aryl group or $C_7$-$C_{20}$ aralkyl group which may be separated by at least one atom selected from oxygen, nitrogen, sulfur and phosphorus, $R^4$ is a $C_1$-$C_{10}$ divalent hydrocarbon group, s is an integer of 0 or 1, d is an integer of 0 to 3, e is an integer of 0 to 3, satisfying d+e=3, and f is an integer of 1 to 300, and an isocyanide compound having the formula (2):

$$Y\text{---}(NC)_q \qquad (2)$$

wherein Y is an optionally substituted, $C_1$-$C_{30}$ monovalent organic group which may be separated by at least one atom selected from oxygen, nitrogen, sulfur and phosphorus, and q is an integer of 1 to 3.

2. The hydrosilylation reaction catalyst of claim 1 wherein in formula (2), q is 1 and in formula (7), s is 0.

3. The hydrosilylation reaction catalyst of claim 1 or 2 which is prepared in a system where hydrosilylation reaction of a compound having an aliphatic unsaturated bond with a hydrosilane compound having a Si—H group or organohydropolysiloxane compound is carried out.

4. The hydrosilylation reaction catalyst of claim 1 wherein L is a monovalent organic group having formula (4).

5. The hydrosilylation reaction catalyst of claim 4 wherein $R^1$ is a $C_1$-$C_5$ alkyl group which may be substituted with halogen.

6. The hydrosilylation reaction catalyst of claim 1 wherein the isocyanide compound having formula (2) is at least one compound selected from the group consisting of mesityl isocyanide, n-butyl isocyanide, t-butyl isocyanide, 1,1,3,3-tetramethylbutyl isocyanide, cyclohexyl isocyanide, 1-isocyanoadamantane, 4-tolyl isocyanide, 1,6-diisocyanohexane, and 1,8-diisocyanooctane.

7. A method for preparing an addition compound comprising the step of carrying out hydrosilylation reaction of a compound having an aliphatic unsaturated bond with a hydrosilane compound having a Si—H group or organohydropolysiloxane compound in the presence of the hydrosilylation reaction catalyst of claim 1.

8. The method for preparing an addition compound of claim 7 wherein the compound having an aliphatic unsaturated bond is an organopolysiloxane having an alkenyl group.

* * * * *